US011872008B2

(12) United States Patent
Jinno

(10) Patent No.: US 11,872,008 B2
(45) Date of Patent: Jan. 16, 2024

(54) MANIPULATOR AND SURGERY SUPPORTING ROBOT SYSTEM

(71) Applicant: Makoto Jinno, Tokyo (JP)

(72) Inventor: Makoto Jinno, Tokyo (JP)

(73) Assignee: Makoto Jinno, Tokyo (JP)

( * ) Notice: Subject to any disclaimer, the term of this patent is extended or adjusted under 35 U.S.C. 154(b) by 824 days.

(21) Appl. No.: 16/860,199

(22) Filed: Apr. 28, 2020

(65) Prior Publication Data

US 2020/0253677 A1    Aug. 13, 2020

Related U.S. Application Data

(63) Continuation of application No. PCT/JP2018/040318, filed on Oct. 30, 2018.

(30) Foreign Application Priority Data

Nov. 1, 2017   (JP) ................................ 2017-211891

(51) Int. Cl.
  *A61B 34/00*   (2016.01)
  *A61B 17/29*   (2006.01)
  *A61B 34/30*   (2016.01)

(52) U.S. Cl.
  CPC .............. *A61B 34/71* (2016.02); *A61B 17/29* (2013.01); *A61B 2034/301* (2016.02)

(58) Field of Classification Search
  CPC . A61B 17/28; A61B 17/29; A61B 2017/2931; A61B 2017/2934;
  (Continued)

(56) References Cited

U.S. PATENT DOCUMENTS

| 5,200,679 A | 4/1993 | Graham |
| 2001/0018591 A1 | 8/2001 | Brock et al. |

(Continued)

FOREIGN PATENT DOCUMENTS

| JP | 2-256489 A | 10/1990 |
| JP | 6-91579 A | 4/1994 |

(Continued)

OTHER PUBLICATIONS

English Translation of JP06091579A (Year: 1994).*

(Continued)

*Primary Examiner* — Darwin P Erezo
*Assistant Examiner* — Erin L Colello
(74) *Attorney, Agent, or Firm* — WHDA, LLP

(57) ABSTRACT

A manipulator includes a first member, a second member that supports the first member such that the first member can rotate about a first rotation axis, a driven portion connected to the first member, which moves on a circumference with respect to the first rotation axis as a center in accordance with a rotation operation of the first member, a flexible member that provides, by a reciprocating operation, a force to drive the driven portion, and a change unit including an arc guide surface, which changes a path of the flexible member in accordance with the rotation operation of the first member. The arc guide surface is arranged to maintain a path length of the flexible member in the reciprocating operation during the rotation operation of the first member.

15 Claims, 26 Drawing Sheets

(58) Field of Classification Search
CPC .............. A61B 34/71; A61B 2034/301; A61B 17/2804; A61B 2017/2927; A61B 2034/715
See application file for complete search history.

(56) References Cited

U.S. PATENT DOCUMENTS

| | | | |
|---|---|---|---|
| 2003/0045888 A1 | 3/2003 | Brock et al. | |
| 2004/0199147 A1 | 10/2004 | Nishizawa et al. | |
| 2012/0143353 A1 | 6/2012 | Kishi | |
| 2016/0303743 A1* | 10/2016 | Rockrohr | B25J 15/0233 |
| 2017/0095236 A1 | 4/2017 | Sharma et al. | |

FOREIGN PATENT DOCUMENTS

| | | | |
|---|---|---|---|
| JP | 06091579 A | * | 4/1994 |
| JP | 2004-122286 A | | 4/2004 |
| JP | 2004-255081 A | | 9/2004 |
| JP | 2006-61364 A | | 3/2006 |
| JP | 2011-200593 A | | 10/2011 |
| JP | 2012-131014 A | | 7/2012 |
| JP | 2013-215509 A | | 10/2013 |
| JP | 2013215509 A | * | 10/2013 |
| JP | 2018-187744 A | | 11/2018 |

OTHER PUBLICATIONS

English Translation of JP2013215509A (Year: 2013).*
Jinno, "Verification of concept of advanced tool of multi-DOF forceps for surgery support robot under laparoscopic surgery (Improvement in arc guide position of simple non-interfering mechanism between pitch and yaw axes)" in Japanese, Proceedings of the 36th academic lecture conference of the Robotics Society of Japan, The Robotics Society of Japan, RSJ2018AC2B1-01, Sep. 7, 2018, vol. 2018, cited in ISR (3 pages).
Jinno, "Verification of concept of advanced tool of multi-DOF forceps for surgery support robot under laparoscopic surgery—Suggestion of simple non-interfering mechanism between pitch and yaw axes", The Proceedings of JSME annual Conference on Robotics and Mechatronics [2424-3124], The Japan Society of Mechanical Engineers, Jun. 5, 2018, vol. 2018, p. 1A1-F01(1)-1A1-F01(4), w/English abstract, cited in ISR (4 pages).
International Search Report dated Jan. 22, 2019, issued in counterpart International Application No. PCT/JP2018/040318 (3 pages).

* cited by examiner

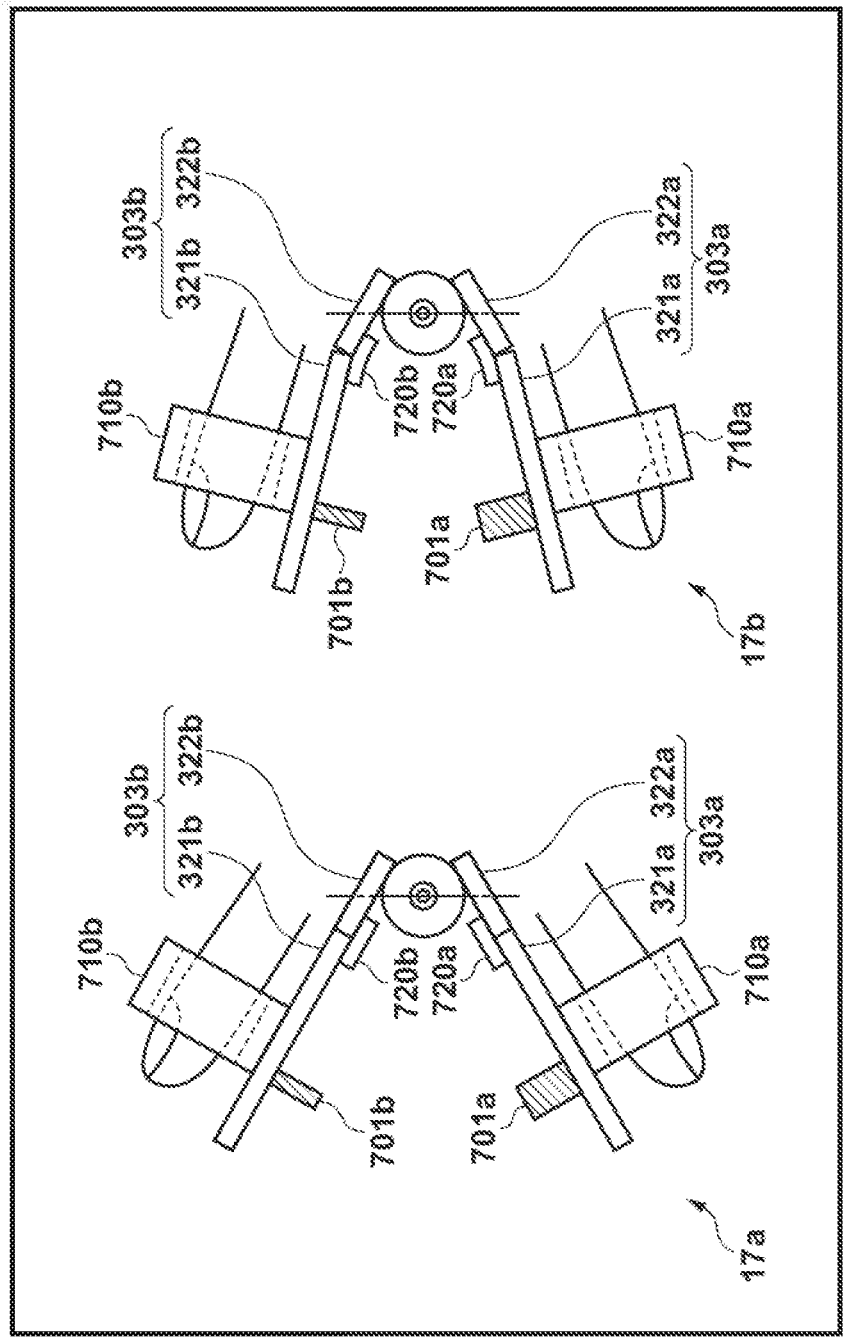

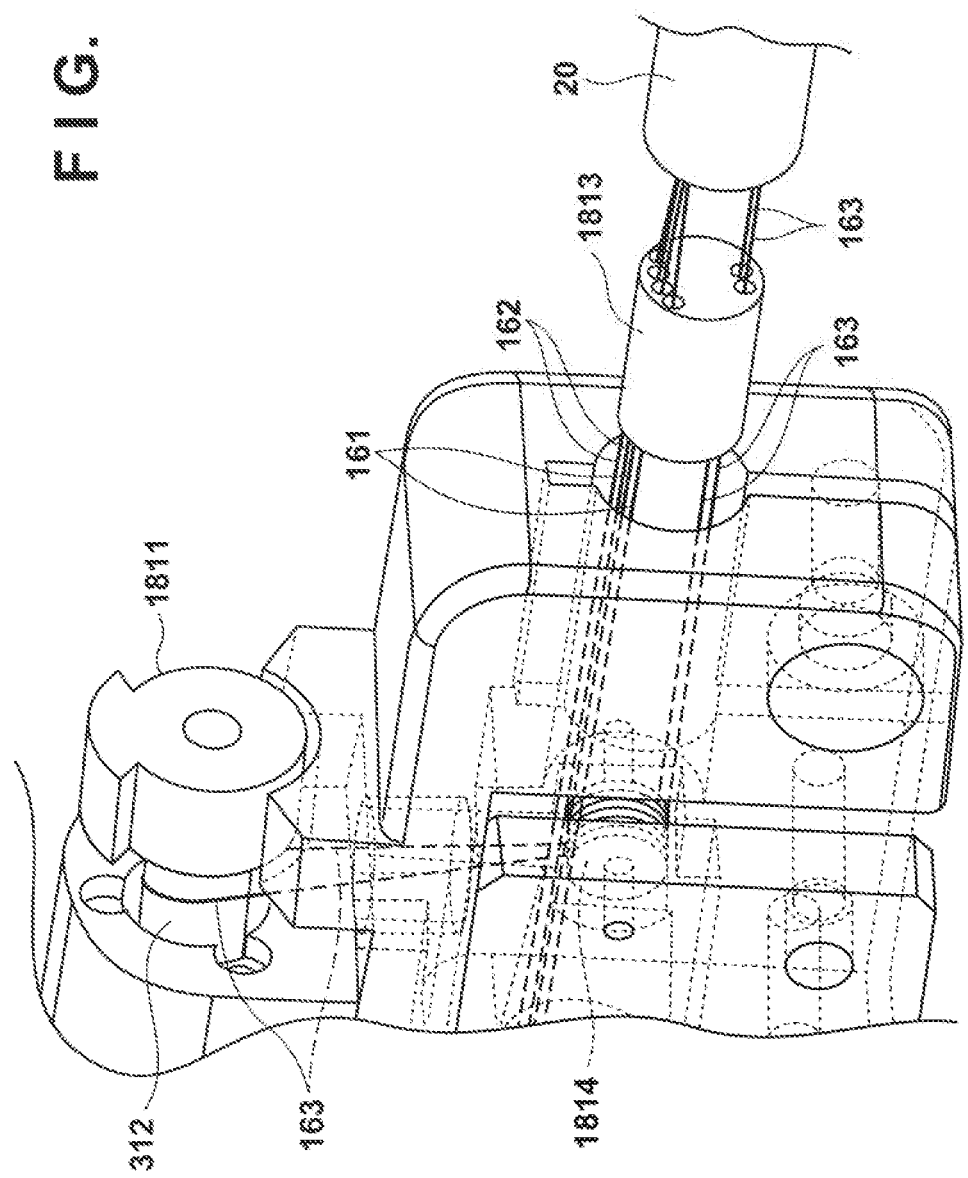

MANIPULATOR AND SURGERY SUPPORTING ROBOT SYSTEM

CROSS-REFERENCE TO RELAIEDAPPLICATION(S)

This application is a continuation of International Patent Application No. PCT/JP2018/040318 filed on Oct. 30, 2018, which claims priority to and the benefit of Japanese Patent Application No. 2017-211891 filed on Nov. 1, 2017, the entire disclosures of which are incorporated herein by reference.

BACKGROUND OF THE. INVENTION

Field of the Invention

The present invention relates to a manipulator and, for example, to a medical manipulator that includes a posture-changeable end effector provided at the distal end of a shaft and is used when conducting a surgical operation, particularly, an endoscopic surgical operation, and a surgery supporting robot system.

Description of the Related Art

In an endoscopic surgical operation (also called a laparoscopic surgery), a plurality of incision holes are made in the abdominal part or the like of a patient, and trocars (tubular tools) are inserted into these incision holes. After that, a laparoscope (camera) and a plurality of pairs of forceps are inserted into the body cavity through the trocars. A gripper used to grip a biotissue, scissors, the blade of an electric scalpel, or the like is attached as an end effector to the distal end portion of each pair of forceps. When the laparoscope and the forceps are inserted into the body cavity, the forceps are operated while viewing the state in the body cavity displayed on a monitor connected to the laparoscope, thereby performing a surgery. Since such a surgery method does not need laparotomy, a burden on a patient is small, and the number of days until recovery after the surgery or discharge is largely decreased. For this reason, such a surgery method is expected to expand the application field.

As the forceps inserted from the trocar, in addition to a general forceps without a joint at the distal end portion, a forceps including a plurality of joints at the distal end portion and capable of changing the posture of the distal end portion, that is, a so-called a medical manipulator has been developed. A medical manipulator described in PTL 1 includes a gripper as an end effector, and can rotate the whole gripper about the pitch axis, rotate the gripper about the yaw axis, and open/close the gripper about the gripper axis (=yaw axis). According to such a medical manipulator, an operation with a high degree of freedom can be performed in a body cavity, the manipulation is facilitated, and cases to which the manipulator can be applied increase.

CITATION LIST

Patent Literature

PTL 1: Japanese Patent Laid-Open No. 2011-200593

However, in the arrangement described in PTL 1, a mechanism interference occurs between the pitch axis and the yaw axis (gripper axis). For example, when the whole gripper is rotated about the pitch axis, rotation about the yaw axis occurs in the gripper accordingly. For this reason, when operating the pitch axis solely, an operation (driving of an actuator) according to the mechanism interference needs to be performed for the yaw axis/gripper axis. That is, when performing rotation about the pitch axis, rotation about the yaw axis (gripper axis) is required to cancel mechanism interference, resulting in complexity of the control system. In addition, adjustment of the gripping force is very important to handle a biotissue. If the mechanism interference exists, it is difficult to mechanically transmit the operation force of a user (a doctor or a surgeon and adjust the gripping force of the end effector (gripper).

The present in provides a technique to reduce or eliminate the occurrence of a mechanism interference in a driven portion driven by a reciprocating operation of a wire.

SUMMARY OF THE INVENTION

According to one aspect of the present invention, there is provided a manipulator comprising: a first member; a second member configured to support the first member such that the first member can rotate about a first rotation axis; a driven portion connected to the first member and configured to move on a circumference with respect to the first rotation axis as a center in accordance with a rotation operation of the first member; a flexible member configured to provide, by a reciprocating operation, a force to drive the driven portion; and a change unit including an arc guide surface configured to change a path of the flexible member in accordance with the rotation operation of the first member, wherein the arc guide surface is arranged to maintain a path length of the flexible member in the reciprocating operation during the rotation operation of the first member.

Further features of the present invention will become apparent from the following description of exemplary embodiments with reference to the attached drawings.

BRIEF DESCRIPTION OF THE DRAWINGS

FIG. 17 is a view showing another arrangement example of the overload preventing mechanism;

FIG. 18B is a view for explaining the path of a wire in the medical manipulator shown in FIG. 18A;

DESCRIPTION OF THE EMBODIMENTS

Embodiments of the present invention will now be described with reference to the accompanying drawings. Note that a medical manipulator will be described below. However, the present invention is not limited to a medical manipulator. In addition, an example in which a gripper is applied as an end effector will be described. However, the present invention is not limited to this. In the following embodiment, an end portion mechanism provided at the distal end portion of a medical manipulator will be described. However, the present invention is not limited to the end portion mechanism. The present invention can be applied to a joint mechanism in which a first member connected to a driven portion driven by a reciprocating operation of a wire is supported by a second member to be rotatable about a first rotation axis.

Figure 9:
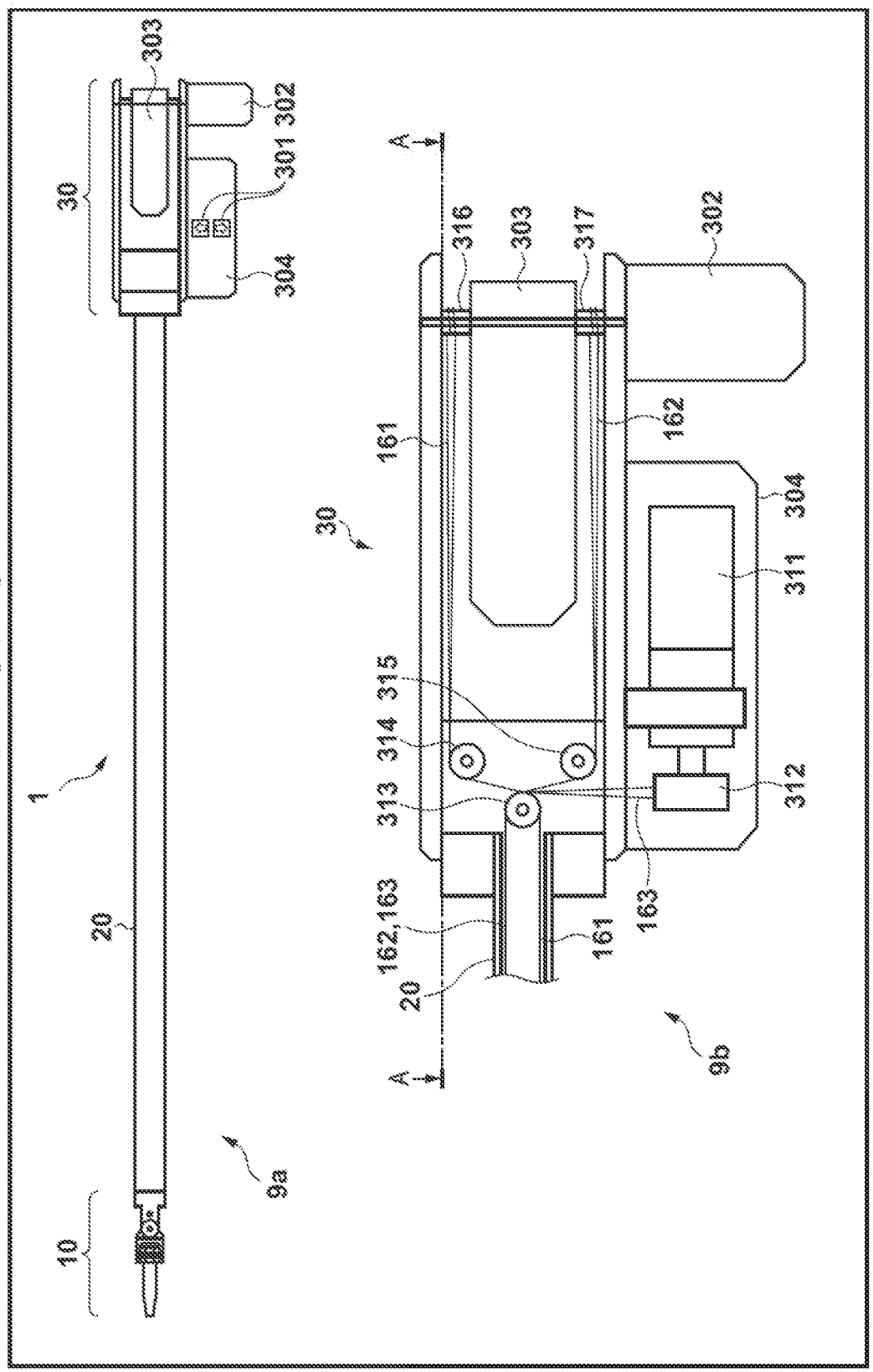
FIG. 9 shows a schematic view (9a) showing the outer appearance of the medical manipulator according to the embodiment and a schematic view (9b) showing the structure of an operation unit.

In FIG. 9, 9a is a view showing the outer appearance of a medical manipulator 1 according to this embodiment. The medical manipulator 1 includes an end portion mechanism 10, a hollow shaft 20, and an operation unit 30. The end portion mechanism 10 is connected to the end portion side of the hollow shaft 20, and the operation unit 30 is connected to the proximal portion side of the hollow shaft 20.

Figure 1:
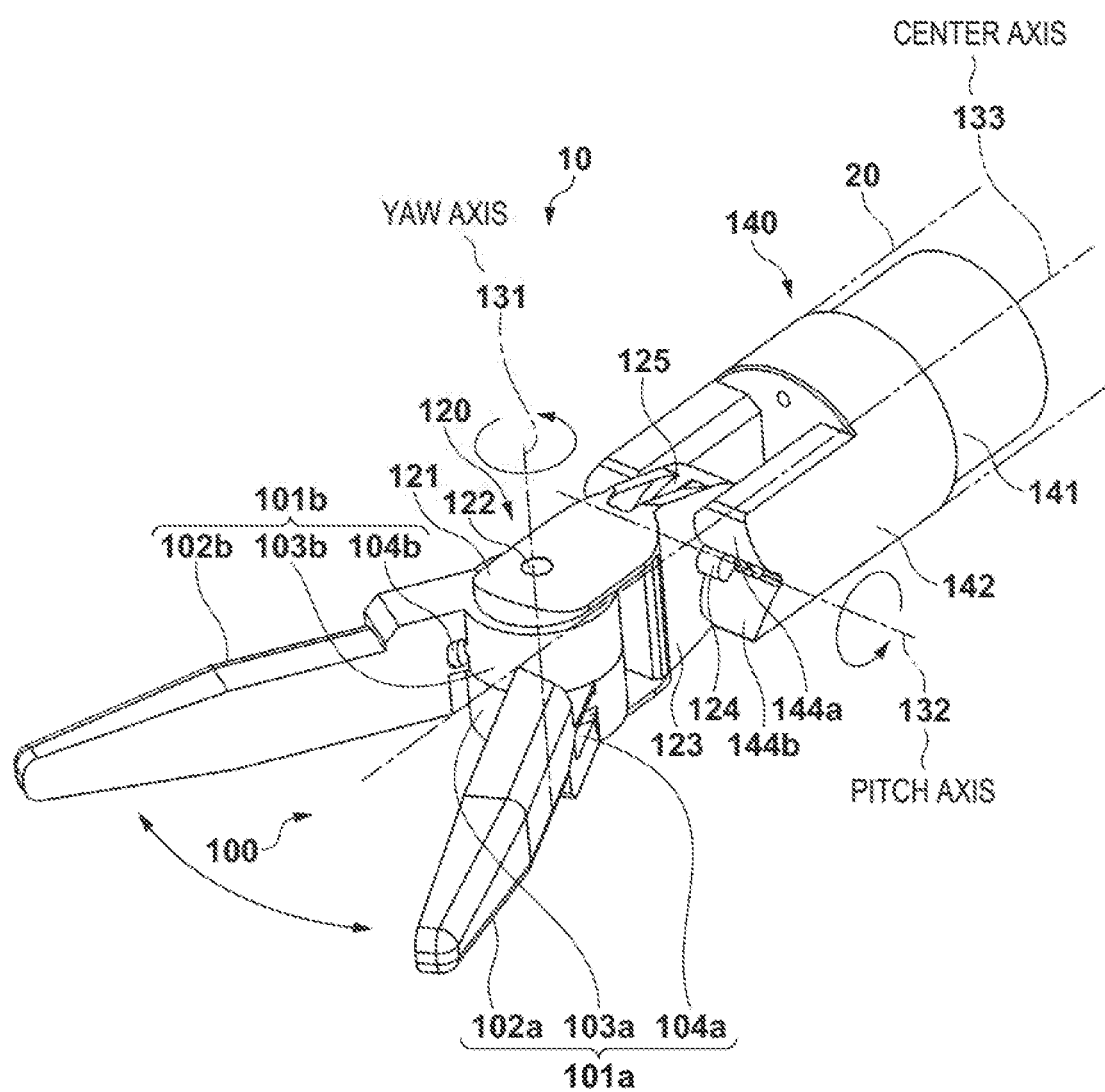
FIG. 1 is a perspective view showing the end portion mechanism of a manipulator according to an embodiment.

FIG. 1 is a perspective view showing the end portion mechanism 10. The end portion mechanism 10 includes a joint mechanism including an end effector 100 serving as a driven portion, a wrist member 120 serving as a first member, and a connecting member 140 serving as a second member. The end effector 100 is provided at the distal end portion of the end portion mechanism 10. The wrist member 120 supports the end effector 100 such that it can rotate about a yaw axis 131 serving as a second rotation axis. The connecting member 140 supports the wrist member 120 such that it can rotate about a pitch axis 132 serving as a first rotation axis and is connected to the hollow shaft 20. Note that the pitch axis 132 is an axis in a direction vertical to a plane including the yaw axis 131 and a center axis 133 that is an axis in the longitudinal direction of the hollow shaft 20. The end effector 100 is connected to the wrist member 120 on the yaw axis 131, and moves on a circumference with respect to the pitch axis 132 as the center in accordance with the rotation operation of the wrist member 120 about the pitch axis 132.

In this embodiment, an example in which a gripper formed by a pair of gripper members 101a and 101b is used as the end effector 100 will be described. Since the gripper member 101a and the gripper member 101b have similar structures, the suffixes will be omitted below if they are not distinguished. A gripper member 101 includes a grip portion 102, a wire guide portion 103, and a wire passage 104. The gripper member 101 is connected to the wrist member 120 by a rotation shaft 122 to be rotatable about the yaw axis 131. This rotation implements the rotation operation of the gripper member 101 in the yaw direction and the opening-closing operation of the gripper member 101. That is, when the gripper member 101a and the gripper member 101b are simultaneously rotated in the same direction, the rotation operation of the end effector 100 about the yaw axis 131 is implemented. Also, when the gripper member 101a and the gripper member 101b are rotated in opposite directions about the yaw axis 131, the opening/closing operation of the gripper is implemented. Hence, in the end portion mechanism 10 according to this embodiment, the yaw axis 131 also serves as a gripper axis. Note that the force for the rotation operation of the gripper member 101 is provided by the reciprocating operations of wires (a first wire 161 and a second wire 162 to be described later with reference to FIG. 3) laid along the wire guide portion 103 through the wire passage 104. Note that as the wires, not only a metal wire of stainless steel or tungsten but also a flexible member such as a fiber-based rope (for example, a Kevlar rope) can be used, but they will be referred to as a wire hereinafter.

The wrist member 120 includes an attachment portion 121 and a rotary support portion 123. The attachment portion 121 supports the end effector 100 (gripper members 101a and 101b) such that it can rotate about the yaw axis 131. More specifically, the attachment portion 121 sandwiches the wire guide portions 103a and 103b of the end effector 100 in the direction of the yaw axis 131 and rotatably holds the wire guide portions 103 by the rotation shaft 122. The rotary support portion 123 has a structure to attach the wrist member 120 to the connecting member 140 such that the wrist member 120 can rotate about the pitch axis 132. More specifically, the rotary support portion 123 includes a projecting portion 124 projecting in the direction of the pitch axis 132, and a wire guide portion 125 on which a wire (a third wire 163 to be described later with reference to FIG. 3) configured to provide a force to rotate the wrist member 120 about the pitch axis 132 is laid. The force to rotate the wrist member 120 is provided by the reciprocating operation of the third wire 163. The projecting portion 124 is rotatably supported by the connecting member 140. Note that in place of the projecting portion 124 of the rotary support portion 123, a structure in which a hole portion is provided in the rotary support portion 123, and the projecting portion 124 is changed to a shaft member to obtain a relationship between a shaft and a hole may be used.

The connecting member 140 includes a connecting portion 141 to be connected to the distal end side of the hollow shaft 20, and a support portion 142 that supports the wrist member 120 such that it can rotate about the pitch axis. FIG.

2 shows the structure of the connecting member 140. A portion with a small outer diameter in the connecting portion 141 is fitted in the inner diameter of the hollow shaft 20. In the support portion 142, a bearing portion 143 rotatably supports the projecting portion 124 of the wrist member 120. A force toward the proximal portion side of the hollow shaft 20 is applied to the wrist member 120 by the wire laid along the wire guide portion 125, and the wrist member 120 is thus rotatably attached to the connecting member 140. Note that if the projecting portion 124 is changed to a shaft member, as described above, the shaft member may be fixed to the bearing portion 143. When the shaft member is fixed, the wrist member 120 is rotatably attached to the connecting member 140 irrespective of the tension of the wire.

The connecting member 140 is provided with through holes 145a to 145f used to pass wires. The outbound path and the returning path of the reciprocating operation of the first wire 161 (FIG. 3) configured to rotate the gripper member 101a about the yaw axis 131 are provided with the through holes 145a and 145c. The outbound path and the returning path of the reciprocating operation of the second wire 162 (FIG. 3) configured to rotate the gripper member 101b about the yaw axis 131 are provided with the through holes 145b and 145d. The outbound path and the returning path of the reciprocating operation of the third wire 163 (FIG. 3) configured to rotate the wrist member 120 about the pitch axis 132 are provided with the through holes 145e and 145f. The through holes 145a to 145f form a communicating portion configured to make the side of supporting the wrist member 120 communicate with the interior of the hollow shaft 20 on the opposite side and pass the wires. Note that the through holes 145a to 145d are provided separately for the paths of the wires. However, the present invention is not limited to this. A structure that forms the paths of the wires cooperatively with arc guide portions 144 at the time of rotation of the wrist member 120 suffices. Hence, for example, a communicating portion configured to pass the wires with respect to the hollow shaft 20, which has an long circular shape, a rectangular shape, or the like formed by connecting the through holes 145a and 145b, suffices.

Each of arc guide portions 144a to 144d includes an arc guide surface configured to change the paths of the wires (the first wire 161 and the second wire 162) used to rotate the end effector 100 about the yaw axis 131 with respect to the wrist member 120. The arc guide surface can have a circular arc shape, an elliptical arc surface, or the like. In this embodiment, an arc shape is applied. The arc guide portions 144a to 144d are arranged while making the arc guide surfaces face each other to sandwich a plane including the center axis 133 and the pitch axis 132 from the upper and lower sides in the communicating portion including the through holes 145a to 145d. The arc guide portions 144a to 144d and the through holes 145a to 145d thus function as a change unit (means) for changing the paths of the wires in accordance with the rotation of the wrist member 120. Note that in this embodiment, the arc guide portions 144a to 144d have guide surfaces of the same shape, and the arc guide portions 144a and 144c and the arc guide portion 144b and 144d are arranged to be symmetric with respect to the plane including the pitch axis 132 and the center axis 133. The through holes 145a to 145d are arranged in parallel to the pitch axis on the plane including the pitch axis 132 and the center axis 133.

Note that in this embodiment, the rotation operation ranges of the wrist member 120 about the pitch axis are equal on both sides of the plane including the pitch axis 132 and the center axis 133, and the guide surfaces of the arc guide portions 144a and 144b and the arc guide portion 144c and 144d are arranged symmetrically. However, as will be described later with reference to FIG. 14, the arc guide portions 144a and 144c and the arc guide portions 144b and 144d need only be arranged to maintain the path length in each of the outbound path and the returning path of the wires during the rotation operation of the wrist member 120. Hence, the arc guide portions 144 need not always be arranged symmetrically, as described above. In addition, the shapes of the guide surfaces may be different from each other. For example, if the rotation operation ranges of the wrist member 120 about the pitch axis are different on both sides of the plane including the pitch axis 132 and the center axis 133, the arc guide portions 144a to 144d are arranged in accordance with the rotation operation ranges, and the shapes of the guide surfaces may be different. Also, if the wrist member 120 rotates only on one side of the plane including the pitch axis 132 and the center axis 133, no arc guide portions need be arranged on the opposite side of the plane. The paths of the wires and the arrangement positions of the through holes 145a to 145d and the arc guide portions 144a to 144d will be described later with reference to FIGS. 4 and 5.

Figure 3:
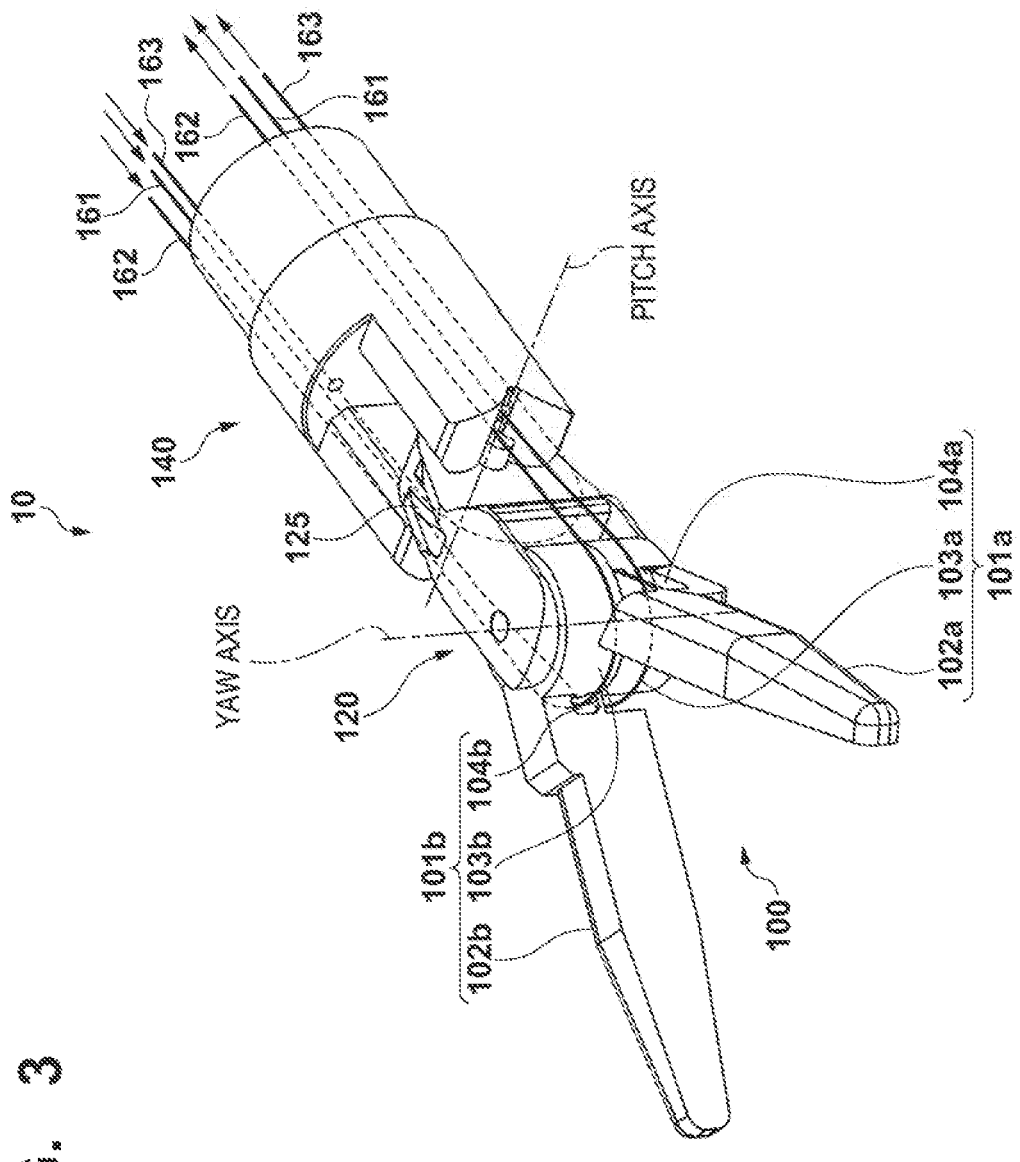
FIG. 3 is a view for explaining the wound states of wires in the manipulator according to the embodiment.

FIG. 3 is a view showing the wound states of wires in the medical manipulator 1 according to this embodiment. The first wire 161 (second wire 162) that transmits the force to rotate the gripper member 101a (101b) about the rotation shaft 122 (yaw axis 131) is laid from the hollow shaft 20 to the outside (the side of supporting the wrist member 120) via the through hole 145a (through hole 145d). The first wire 161 (second wire 162) is wound around the wire guide portion 103a (103b) through a wire passage 104a (104b). In FIG. 3, the first wire 161 (second wire 162) is wound about a half round on the wire guide portion 103a (103b). However, the wire is preferably wound almost one and half round. In addition, at least a part of the first wire 161 (second wire 162) is fixed to the wire guide portion 103a (103b), thereby enabling power transmission without slip of the wire. The first wire 161 (second wire 162) enters the hollow shaft 20 again via the through hole 145c (145b). By the reciprocating operation of the first wire 161 (second wire 162), the gripper member 101a (101b) rotates about the yaw axis 131. As described above, the first wire 161 and the second wire 162 individually rotate the pair of gripper members 101a and 101b about the yaw axis 131.

The third wire 163 is laid from the inside of the hollow shaft 20 to the outside (the side of supporting the wrist member 120) via the through hole 145e, wound around the wire guide portion 125, and returned from the through hole 145f to the inside of the hollow shaft 20. By the reciprocating operation of the third wire 163, the wrist member 120 rotates about the pitch axis 132 with respect to the connecting member 140. In FIG. 3, the third wire 163 is wound about a half round on the wire guide portion 125, like the first wire 161 and the second wire 162. However, the wire is preferably wound almost one and half round. In addition, at least a part of the thud wire 163 is fixed to the wire guide portion 125, thereby enabling power transmission without slip of the wire. As described above, the wrist member 120 is pulled by the third wire 163 to the proximal portion side of the hollow shaft 20, and the projecting portion 124 is thus pressed against the bearing portion 143 and supported by the connecting member 140.

According to the above-described structure, when the wrist member 120 rotates about the pitch axis 132, the directions of the first wire 161 and the second wire 162 are changed by the arc guide portions 144. However, as will be described later, the path change by the arc guide portions 144 can minimize that the changes in the path lengths of the first wire 161 and the second wire 162 can be set to such degree that the changes can be ignored. It is therefore possible to obtain a joint mechanism in which a force (mechanism interference) to rotate the gripper member 101 is not generated even the wrist member 120 rotates.

Figure 14:
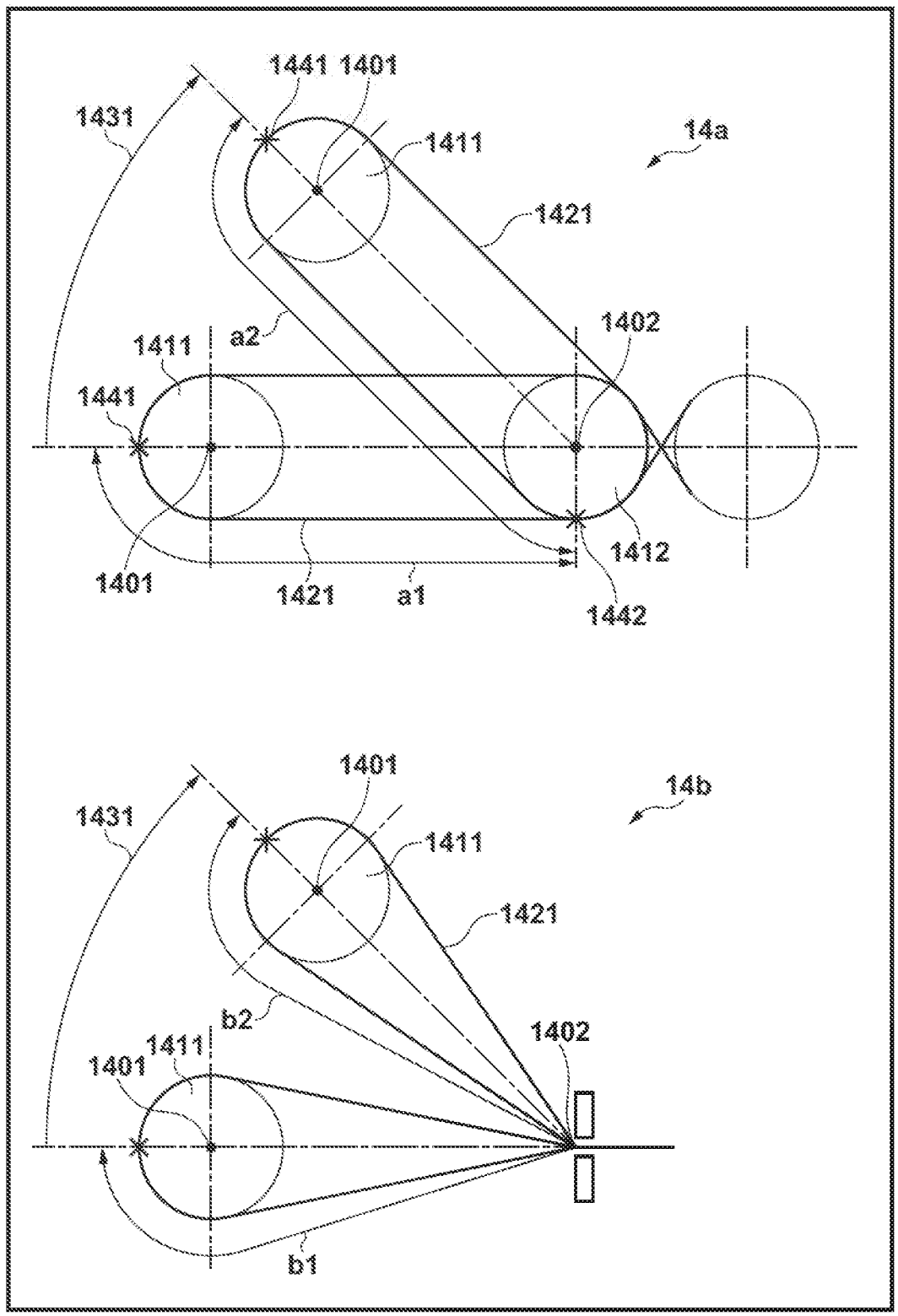
FIG. 14 is a view for explaining a change in the path length of a wire and a mechanism interference.

FIG. 14 is a view for explaining a change in the path length and a mechanism interference. Note that in FIG. 14, the pitch axis corresponds to a rotation axis 1402, and the yaw axis corresponds to a rotation axis 1401. For easy understanding of the description, a case in which the rotation axis 1401 and the rotation axis 1402 are axes parallel to each other is shown. In FIG. 14, 14a shows a case in which the path of a wire 1421 is formed by a first pulley 1411 that rotates about the rotation axis 1401 and a second pulley 1412 that rotates about the rotation axis 1402, as in the arrangement of PTL 1. The outbound path and the returning path of the wire 1421 are defined based on a distal end position 1141 of the first pulley 1411 as a boundary. If rotation about the rotation axis 1402 occurs, as indicated by an arrow 1431, the path length of the wire 1421 from the distal end position 1441 of the first pulley 1411 to a position 1442 of the second pulley 1412 changes from a path length a1 to a path length a2. As a result, a position corresponding to the path length a1 after the rotation deviates from the distal end position 1441, and a rotation about the rotation axis 1401 occurs in the first pulley 1411. If the ratio of the path lengths of the outbound path and the returning path of the wire varies between the first pulley 1411 that rotates about the rotation axis 1401 and the second pulley 1412 at the preceding stage, a mechanism interference occurs.

Figure 2:
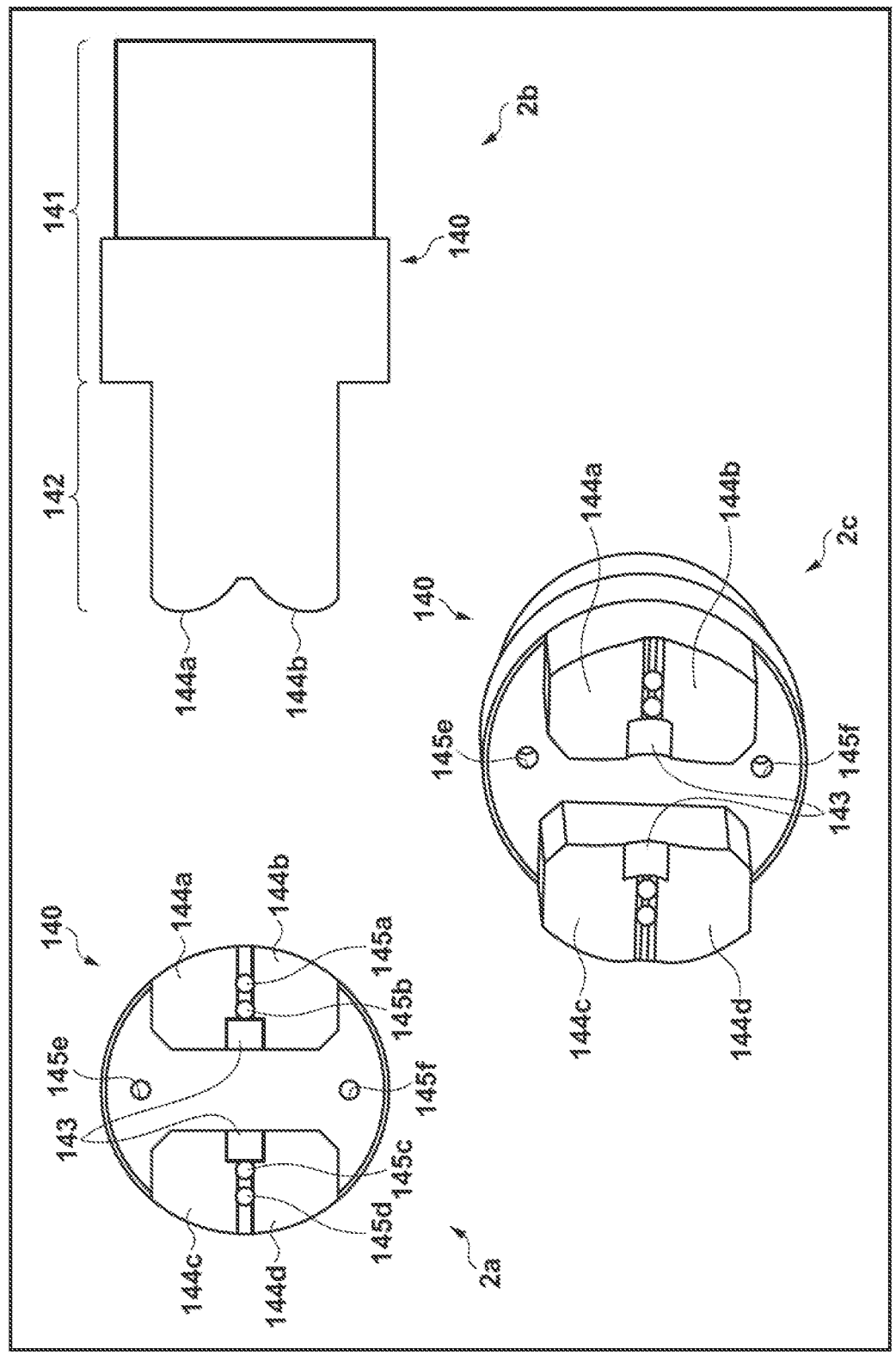
FIG. 2 is a view for explaining the structure of a connecting member that constitutes the end portion mechanism.

On the other hand, in 14b of FIG. 14, the wire 1421 is bent at the position of the rotation axis 1402. In this case, a path length b1 of the outbound path of the wire 1421 before the rotation and a path length b2 of the outbound path of the wire 1421 after the rotation equal. Since the path lengths of the outbound path and the returning path and the ratio of the path lengths do not change (the path lengths of the outbound path and the returning path are maintained), rotation about the rotation axis 1401 of the first pulley 1411 does not occur. However, since the wire 1421 cannot be bent as in FIG. 14b, in this embodiment, the arc guide portions 144a to 144d are arranged to change the path. As shown in FIGS. 1 and 2, in this embodiment, the through holes 145a to 145d are provided to be arranged in parallel to the pitch axis 132 on the plane including the pitch axis 132 and the center axis 133. The arc guide surfaces of the arc guide portions 144a to 144d are provided not to change the path lengths of the outbound path and the returning path of each wire and the ratio of the path lengths. That is, the guide surfaces are arranged to maintain the path lengths of the outbound path and the returning path in the reciprocating operation of each wire (such that the path lengths change to such a degree that the changes can be ignored). Note that maintaining the path length means that, for example, the change in the path length is absorbed by expansion/contraction of the wire and does not affect the end effector 100, or the change in the path length is suppressed to such a degree that its influence can be ignored.

By the appropriate arrangement of the through holes 145a to 145d and the arc guide portions 144a to 144d as described above, the end portion mechanism 10 (joint mechanism) in which a mechanism interference is almost absent between the pitch axis and the yaw axis (gripper axis can be obtained. For this reason, rotations about the pitch axis and the yaw axis in the end portion mechanism 10 can easily be controlled, and high controllability can be obtained. In addition, it is possible to provide a robot forceps that is totally manually driven or hybrid-driven manually and by a motor. Such a robot forceps will be described later with reference to FIG. 9. According to the end portion mechanism 10 of this embodiment, the number of pulleys decreases, and the number of shafts configured to support the pulleys also decreases as a matter of course. That is, the number of components greatly decreases as is apparent from comparison with the arrangement of PTL 1. Hence, the component cost and the manufacturing cost of the end portion mechanism 10 are reduced. In addition, since the manipulator can be provided inexpensively, a disposable manipulator can also be provided.

In addition, the end portion mechanism 10 has an arrangement in which a pulley using the pitch axis 132 as the center does not exist, and a pulley does not intervene between the yaw axis 131 and the pitch axis 132, the distance (offset) between the yaw axis 131 and the pitch axis 132 can be made small. As a result, it is possible to implement a manipulator having a small turning radius and easy to use.

The through holes 145a to 145f have airtightness capable of maintaining a pneumoperitoneum pressure of 5 to 20 mmHg in a state in which the wires are inserted into them. Hence, in the whole medical manipulator 1 as shown in FIG. 9, the airtightness to maintain the pneumoperitoneum pressure need not be ensured, and the medical manipulator 1 can be provided easily and inexpensively. Note that if the connecting member 140 and the wire members are made of a metal such as stainless steel, and airtightness can hardly be ensured, a rubber member with a through hole whose diameter is smaller than that of the through hole 145 capable of passing wires may be provided on the proximal portion side of each through hole 145, or a resin-coated wire may be used.

If the wrist member 120 rotates about the pitch axis, the passages of the first wire 161 and the second wire 162 are arranged along the arc guide surfaces of the arc guide portions 144. Hence, even if the wrist member 120 rotates about the pitch axis, and the directions of the wires are changed, the wires are not bent. The gripper member 101 can smoothly be moved in a state in which the bending radii of the wires are ensured, and the life of the wires can greatly be prolonged. Additionally, in a case in which a pulley is used as each arc guide portion, to arrange the pulley such that it fits in the outer diameter of the connecting member 140, the pulley diameter needs to be reduced, and it is therefore difficult to sufficiently ensure the bending radius of each wire. Note that the diameter of each wire guide portion 103, the diameter of the wire guide portion 125, and the diameter of the arc guide surface of each of the arc guide portions 111a to 144d are appropriately decided based on the relationship between the size required of the end portion mechanism 10, the diameter of the wound wires, and the necessary durability (the life of the wires).

On the other hand, if the center position or radius of the circular arc shape of the guide surface is not appropriate, the path lengths of the first wire 161 and the second wire 162 change depending on the angle of the wrist member 120. The variation amounts of the path lengths of the first wire 161 and the second wire 162 change using, as parameters, the center and radius of the circular arc shape of the guide surface of each arc guide portion 144. The center and radius of the arc guide surface are preferably selected such that the variations in the path lengths of the wires become as small as possible. Hence, from the above-described viewpoint of suppressing the variations in the path lengths of the wires in a case in which the arc guide portions 144 each having a guide surface with a circular arc shape as an arc guide surface are used, appropriates parameters concerning the arrangement of the arc guide portions 144 will be described.

Figure 4:
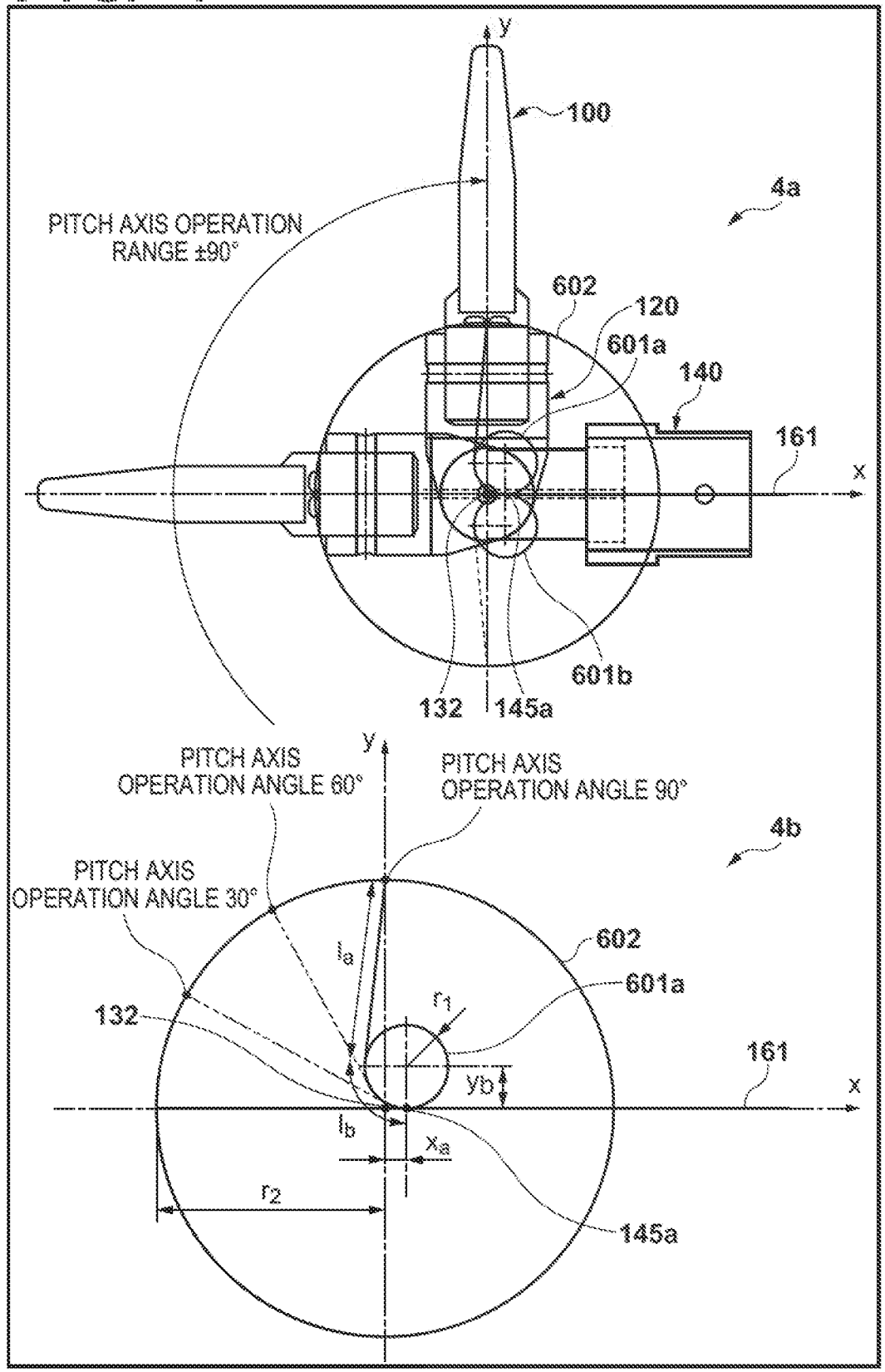
FIG. 4 is a view for explaining the arrangement of arc guide portions.

FIG. 4 is a view for explaining the rotation operation of the wrist member 120 (end effector 100) with respect to the pitch axis as the center and the variation in the path length of a wire (to be referred to as a wire length error hereinafter).

In FIG. 4, 4a is a view showing a change in the path of the first wire 161 in a case in which the pitch axis is set in the vertical direction with respect to the sheet surface. FIG. 4a shows a change in the path in a case in which the wrist member 120 supporting the end effector 100 rotates by 90° about the pitch axis. Circles 601 each forming the circular arc-shaped guide surface of an arc guide portion 144 are illustrated in a superposed manner, and a circle 602 whose radius corresponds to the distance from the center of the pitch axis 132 to the wire guide portion 103 is illustrated. The circle 602 shows a circumference on which the end effector 100 (wire guide portion 103) moves when the wrist member 120 rotates about the pitch axis 132. As the coordinate system, a coordinate system in which, on a plane perpendicular to the pitch axis 132, the position of the pitch axis 132 is defined as the origin, and axes that pass the origin and are orthogonal to each other are defined as an x-axis and a y-axis is used. In addition, a plane including the x-axis and the y-axis will be referred to as an xy-plane. In particular, in FIG. 4a, a coordinate system in which the center axis 133 that is the axis in the longitudinal direction of the hollow shaft 20 matches the x-axis is set. That is, on the plane including the center axis 133 and perpendicular to the pitch axis, the pitch axis rotation center is defined as the origin (0, 0) the center axis 133 is defined as the x-axis, and an axis orthogonal to the x-axis at the origin position is defined as the y-axis. The centers of a circle 601a and a circle 601b are arranged in parallel in the y-axis direction, and the through holes 145a to 145d are arranged on a line that passes the intersection between the line connecting the centers and the x-axis and is set in the direction perpendicular to the xy-plane.

FIG. 4b is a view showing the circle 601a and the circle 602 in FIG. 4a, and schematically shows the path of the first wire 161 and the position of the through hole 145a (145c). A radius $r_1$ of the circle 601a has a magnitude obtained by adding ½ of the diameter of the wire to the radius of the arc guide portion 144, and the center coordinates are $(x_a, y_b)$. When $y_b=r_1$ is set, the center axis of the hollow shaft 10 and the circle 601a are in contact. Hence, from the viewpoint of preventing bending of the wire, $y_b=r_1$ or $-r_1$ is preferable. In addition, the radius of the circle 602 is set to $r_2$. If the rotation angle of the wrist member 120 is 0° with respect to the -x-axis, the length from the position (coordinates $(x_a, 0)$) of the through hole 145a to the circumference of the circle 602 is $r_2+x_a$. The paths of the wire when the rotation angle (to be referred to as a pitch axis operation angle hereinafter) of the wrist member 120 about the pitch axis is 30°, 60°, and 90° are as shown in FIG. 4. Except for the pitch axis operation angle=0°, the length from the coordinates $(x_a, 0)$ to the circumference of the circle 602 is the sum of a length $l_a$ from the circumference of the circle 602 to the contact of the wire on the circumference of the circle 601a and a length $l_b$ up to the coordinates $(x_a, 0)$ along the circumference of the circle 601a. Hence, the wire length error e is defined as $e=(r_2+x_a)-(l_a+l_b)$.

Figure 6:
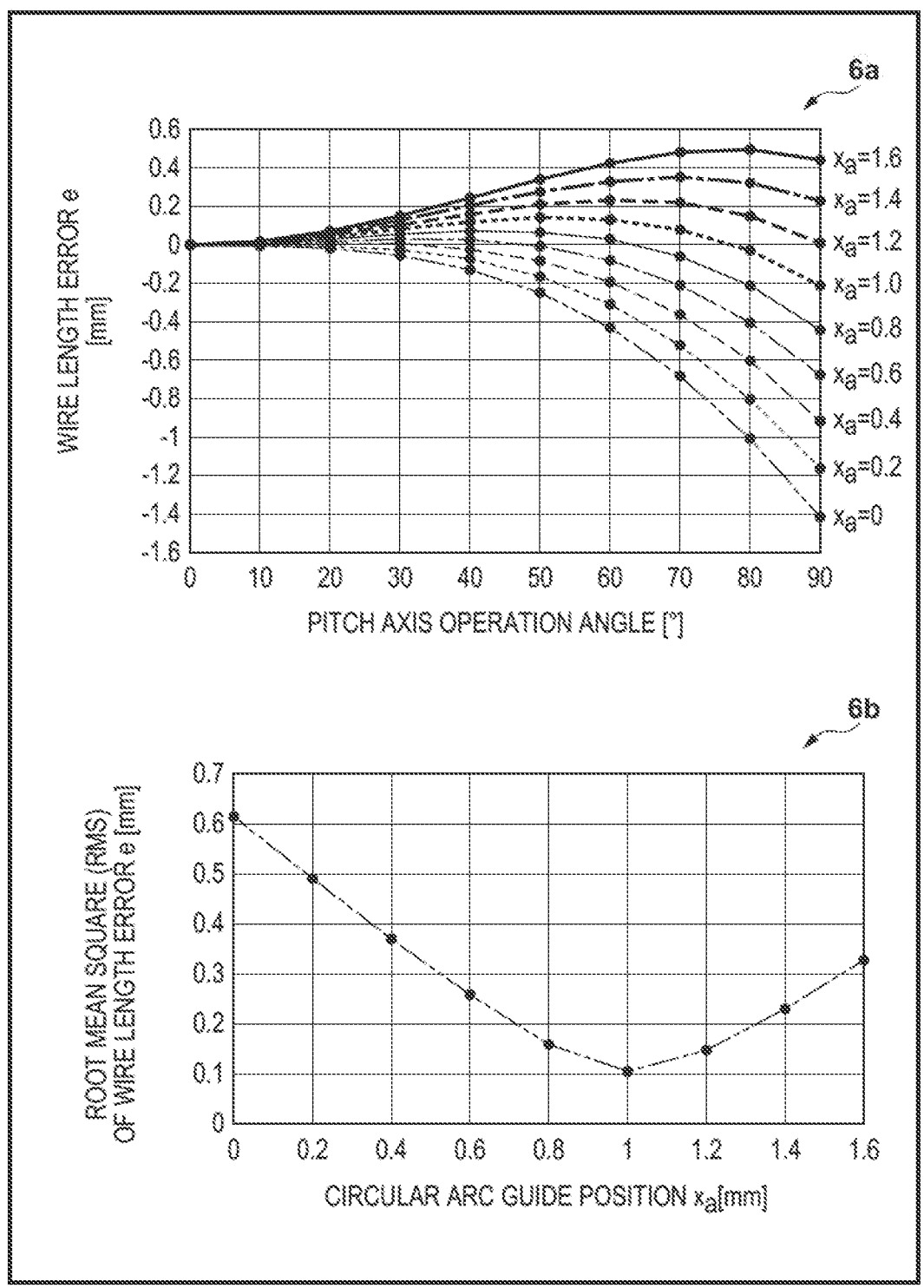
FIG. 6 is a view showing an example of a calculation result concerning a wire length error e.

In FIG. 6, 6a is a graph showing a result of calculating, for different x-coordinate values $x_a$, a change in the wire length error e within the pitch axis operation angle range of 0° to 90° with respect to -x axis when $r_1=2$ mm, $r_2=9.2$ min, and $y_b=r_1=2$ mm. In this example, $x_a$ is changed every 0.2 mm from 0 to 1.6 mm. For any x-coordinate value, the wire length error e changes in accordance with the pitch operation angle. In FIG. 6, 6b is a graph showing a result of calculating, for each value $x_a$, the root mean square (RMS) of the wire length error e within the pitch operation angle range of 0° to 90°. As is apparent from this graph, the RMS of the wire length error e within the pitch axis operation angle range of 0° to 90° is minimized when $x_a=1$. Hence, $x_a$ and $y_b$, which minimize the RMS of the wire length error e, are $$x_a=r_1/2, \text{ and } y_b=r_1 \text{ or } -r_1 \qquad (1)$$

Hence, when the arc guide portion 144 having a circular arc-shaped surface with the radius $r_1$ (strictly, a radius obtained by subtracting ½ of the wire diameter from $r_1$) with respect to the position $(x_a, y_b)$ represented by equations (1) as the center is used, the wire length error when the wrist member 120 is rotated about the pitch axis 132 can be minimized.

Figure 7:
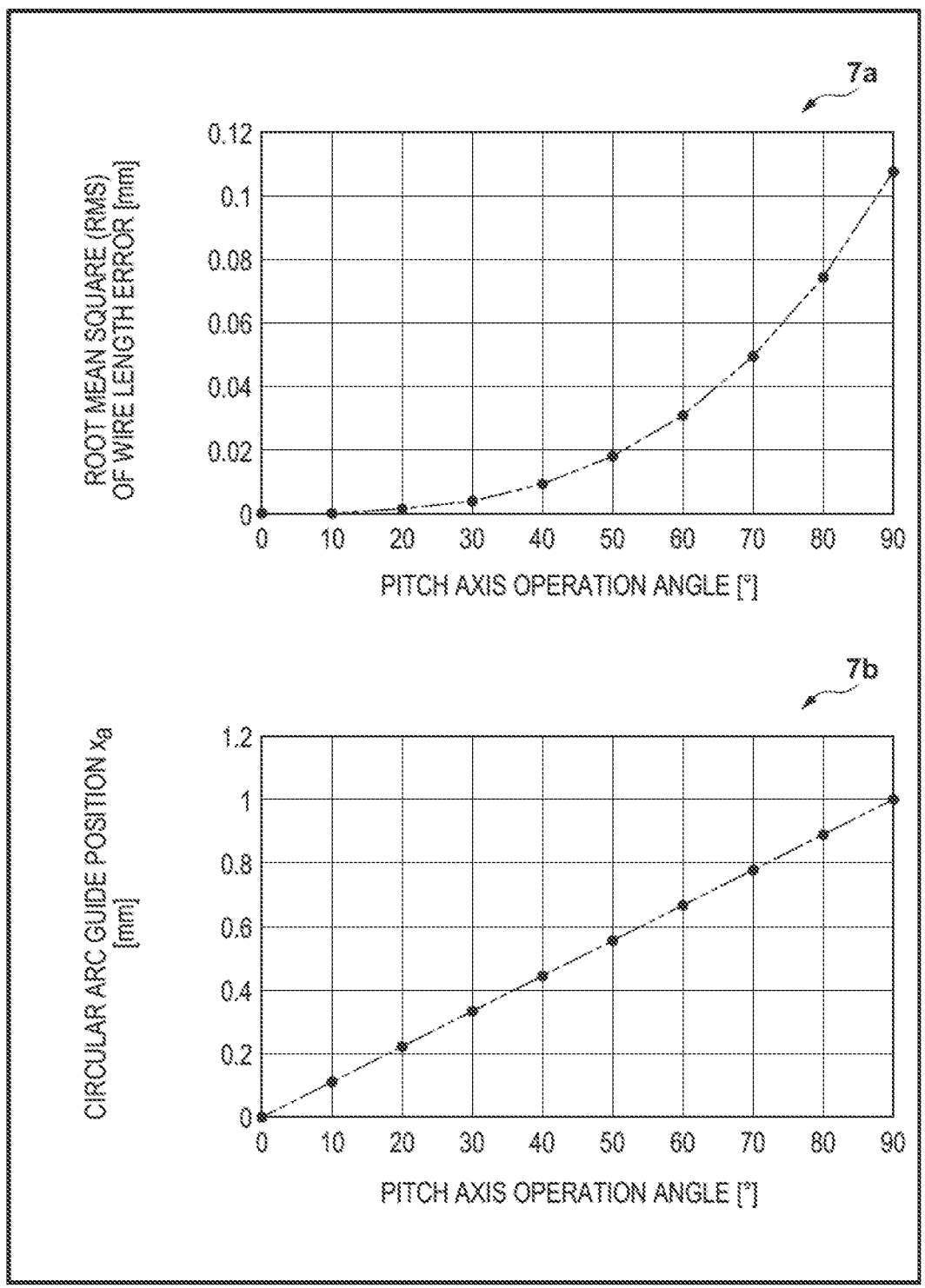
FIG. 7 is a view showing an example of a calculation result concerning the wire length error e.

Note that if the range of the pitch axis operation angle is smaller than 90°, the value of the RMS of the wire length error e changes in accordance with the range. In FIG. 7, 7a shows the relationship between the upper limit value of the pitch axis operation angle and the minimum value of the value of the RMS of the wire length error e. In FIG. 7, 7b is a graph showing the relationship between the upper limit of the pitch axis operation angle and the x-coordinate of the center position of the circle 601a at which the RMS of the wire length error e has the minimum value. As is apparent from FIG. 7b, in a case in which the upper limit of the range of the pitch axis operation angle, that is, the maximum angle of the rotation operation of the wrist member 120 about the pitch axis 132 is n°(|n|≤90) with respect to the -x-axis, when $$x_a=(r_1/2)(|n|/90), \text{ and } y_b=r_1 \text{ or } -r_1 \qquad (2)$$

the RMS of the wire length error e is minimized.

Note that the average value of the absolute values of the wire length errors also has almost the same tendency. Hence, if the range of the pitch axis operation angle is n° with respect to the -x-axis, the arc guide portion 144 having a circular arc-shaped surface with the radius $r_1$ (strictly, a radius obtained by subtracting ½ of the wire diameter from $r_1$) with respect to the position $(x_a, y_b)$ represented by equations (2) as the center is preferably used. In this case, the position of the through hole 145a on the end side is represented by $(x_a, 0)$. Note that similar effects can be obtained when a pulley is used as the arc guide portion. The maximum angle of rotation with respect to the -x-axis may be different in the positive direction and the negative direction. In this case, the x-coordinate obtained from equations (2) has a different value. Hence, the two opposing arc guide portions 144a and 144b and the arc guide portions 144c and 144d are not symmetrical with respect to the pitch axis 132 or a plane including the pitch axis 132 and the center axis 133.

As is apparent from FIG. 6b, within the range of ±30% ($0.7x_a$ to $1.3xa$) with respect to $x_a=(r_1/2)$, the RMS of the wire length error e is 0.2 mm or less. This can suppress the error to about 2% or less for $r_2+x_a=9.2+1=10.2$ mm. Hence, a preferable example of the range of $x_a$ is $0.7\times(r_1/2) \leq x_a \leq 1.3\times(r_1/2)$. However, the present invention is not limited to this. As for $y_b$, $y_b \approx r_1$ is preferable within the range where a working error or a smooth operation of the wire is not impeded.

The optimum arrangement of the arc guide portions 144 has been examined above. In FIG. 4, the y-coordinate of the center position of the circular arc shape is fixed to the radius $r_1$ of the circle 601a from the viewpoint of maintaining the continuity in the connecting portion between the through holes 145 and the arc guide portions 144 to prevent bending of the wires. However, the present invention is not limited to this, and y may be smaller than $r_1$. This will be described with reference to FIG. 5.

Figure 5:
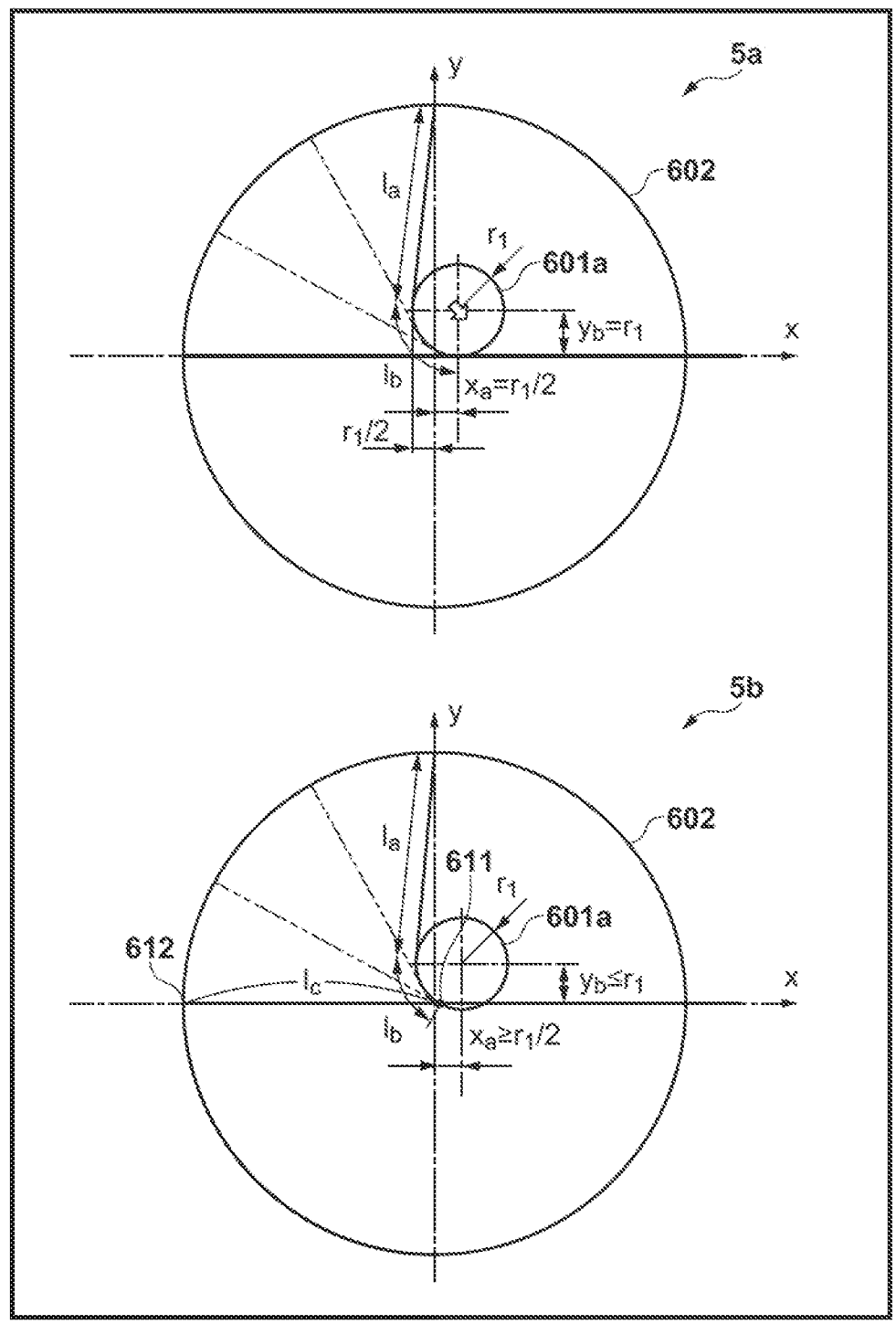
FIG. 5 is a view for explaining the arrangement of arc guide portions.

In FIG. 5, 5a shows the circle 601a arranged in accordance with equations (1) described above, and the coordinates of the center position are $(x_a=r_1/2, y_b=r_1)$. A state in which the center position of the circle 601a has been moved in a direction of increasing the x-coordinate and decreasing the y-coordinate from the above-described coordinates is shown in 5b of FIG. 5. Note that in the case of the center position of the arc guide portion 144 in the fourth quadrant, the center position is moved in a direction of increasing the y-coordinate. An intersection 611 between the circle 601a and the x-axis on the end side (the side of the wrist member 120) is the position of the through hole 145a. Letting $l_a$ be the length from the circumference of the circle 602 to the contract of the wire on the circumference of the circle 601a, $l_b$ be the distance from the contact of the wire on the circle 601a to the intersection 611, and $l_c$ be the length from an intersection 612 between the circle 602 and the x-axis to the intersection 611, the wire length error e can be defined as $e=l_c-(l_a+l_b)$.

Figure 8:
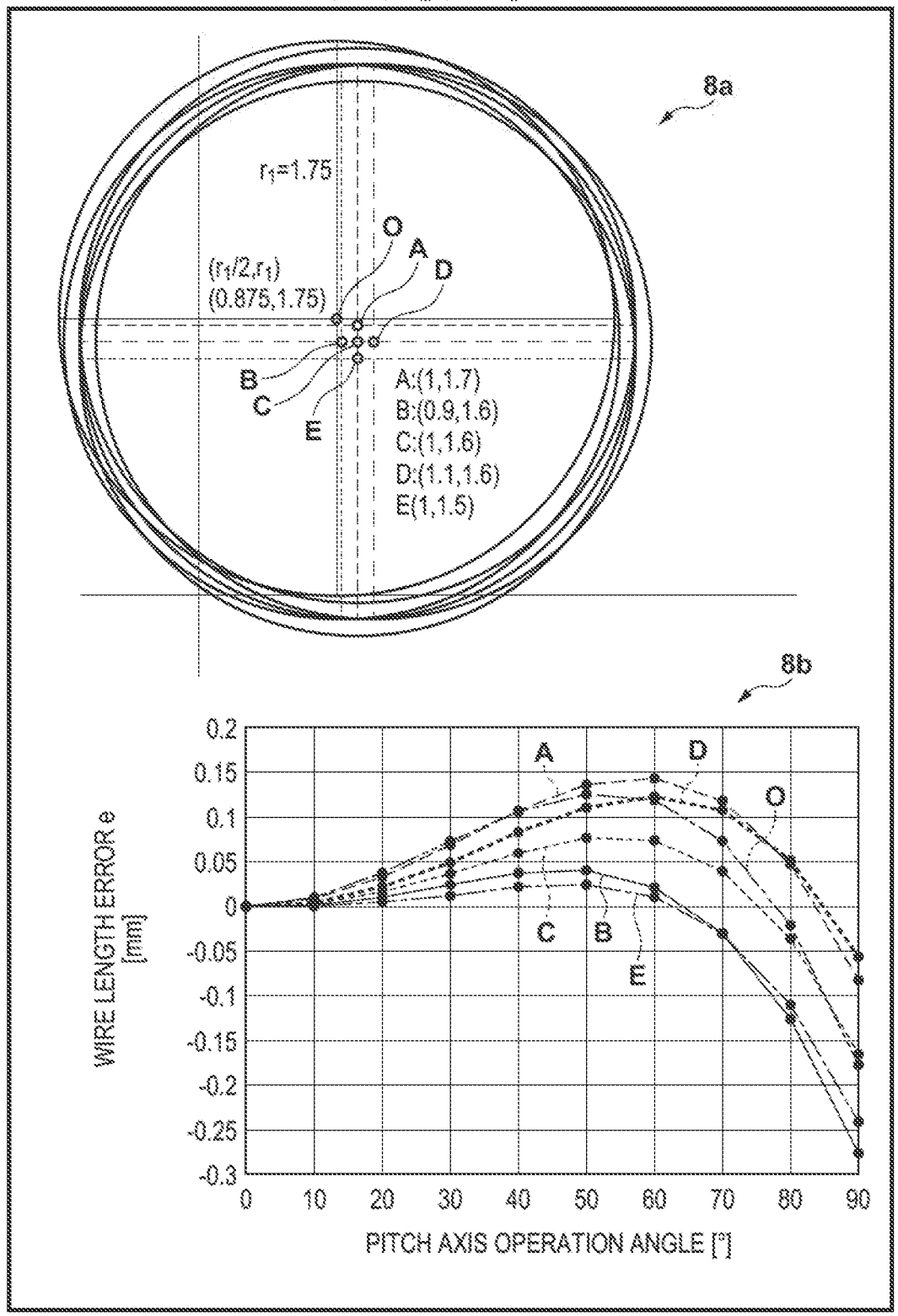
FIG. 8 is a view showing an example of a calculation result concerning the wire length error e.

FIG. 8 shows a calculation example of the wire length error e. In FIG. 8, 8a shows coordinates O and A to E of the center position (the center position of the circle 601a) of the circular arc shape used for the calculation. In this example, $r_1=1.75$, and the coordinates O are $(r_1/2, r_1)=(0.875, 1.75)$ obtained by equations (1) or (2) described above. The coordinates A to E are (1, 1.7), (0.9, 1.6), (1, 1.6), (1.1, 1.6), and (1, 1.5), respectively. The relationship between the wire length error e and the pitch axis operation angle in a case in which the coordinates O and the coordinates A to E are set to the center position is shown in 8b of FIG. 8. When the RMS of the wire length error e is plotted and calculated for each of the coordinates of the center position of the circular arc shape, an RMS smaller than in the case of the coordinates O is obtained in the case of the coordinates A to E. That is, generally, as compared with the state shown in FIG. 4b (when the center position of the circular arc shape has the coordinates O $(x_a=r_1/2, y_b=r_1)$), a smaller RMS on be obtained when the center position of the circular arc shape is represented by the coordinates A to E in FIG. 8a. Hence, it is found that $$x_a > (r_1/2), \text{ and } y_b < r_1 \text{ or } y_b > -r_1 \quad (3)$$

may be set. As is also apparent, when the maximum angle of the rotation operation is $|n|°$ as in equations (2), $$x_a > (r_1/2)(n/90), \text{ and } y_b < r_1 \text{ or } y_b > -r_1 \quad (4)$$

may be set.

Note that when the coordinates $(r_1/2, r_1)$ are set to (0.875, 1.75), the RMS of the wire length error e is minimized when the coordinates of the center position of the circle 601a are almost (1, 1.6). In the above-described example, the wire length error is obtained for the coordinates (1.1, 1.6) with the maximum x-coordinate and the coordinates (1, 1.5) with the minimum y-coordinate. If the center position of the circle 601a exists within this range, the wire length error e is smaller than in a case in which the center position is at (0.875, 1.75). Hence, for example, if $x_a=r_1/2$ to $+30\%$, and $y_b=r_1$ to $-30\%$, the upper limit value of the x-coordinate and the lower limit value of the y-coordinate are (1.14, 1.23). All the coordinates A to E fall within this range, and the RMS of the wire length error e becomes small within this range. Hence, the upper limit value of the x-coordinate and the lower limit value (in the fourth quadrant, the lower limit value) of the y-coordinate in equations (3) and (4) may be set as follows. That is, concerning equation (3), $$x_a < (r_1/2) \times 1/3 (\approx 1.14),$$

$$y_b > r_1 \times 0.7 (\approx 1.23), \text{ or } y_b < -r_1 \times 0.7 (\approx -1.23)$$

hold. Alternatively, concerning equation (4), $$x_a < (r_1/2)(|n|/90) \times 1.3,$$

$$y_b > r_1 \times 0.7 (\approx 1.23), \text{ or } y_b < -r_1 \times 0.7 (\approx -1.23)$$

hold. Note that a numerical value represented by $\approx$ in parentheses is a value in a case in which the center position is at $(r_1/2=0.875, r_1=1.75)$.

Note that the above description has been made assuming that the maximum operation angle of the pitch axis is $n°$. The maximum angle of a main operation in actual use may be taken into consideration. For example, even in a case in which the designed operation region is $\pm 90°$, if the main operation region is $\pm 80°$, determination may be done by considering the RMS of the wire length error e in this range. For example, even in a case in which the RMS when $n°=90°$ is not minimum, if the RMS when $n°=80°$ becomes smaller, the position at which the RMS when $n°=80°$ is minimum may be set to the center position of the circular arc shape. The examination example shown in FIG. 8 above shows that the RMS is minimized when the circle 601a is arranged at the coordinates C (1, 1.6) when n=90. However, near the coordinates (1, 1.55), the RMS when $n°=90°$ is minimum but sufficiently small. Further, the RMS when $n°=80°$ is smaller. Hence, even in a case in which the designed operation region is $\pm 90°$, if the main operation region is $\pm 80°$, the circle 601a may be arranged with respect to the coordinates (1, 1.55) as the center.

Note that although bending of the wire occurs at the intersection 611 (the outlet of the through hole 145), the influence exerted on the life of the wire is small because the angle of bending is air obtuse angle. Preferably, the angle made by the x-axis and the tangent of the circle 601a at the intersection between the x-axis and the circle 601a is set to 30° or less. To implement smoother passage of the wire at the intersection 611, rounding for eliminating the edge of bending portion at the intersection 611, that is, the through holes 145a to 145d may be performed. Hence, when the guide surface of the arc guide portion 144 is set as represented by equation (2), the variation in the path length of the wire can be made very small. Such an arrangement of the circular arc shape cannot be implemented by a structure using a pulley. This is one of the effects obtained by employing the arc guide portion 144.

Figure 22:
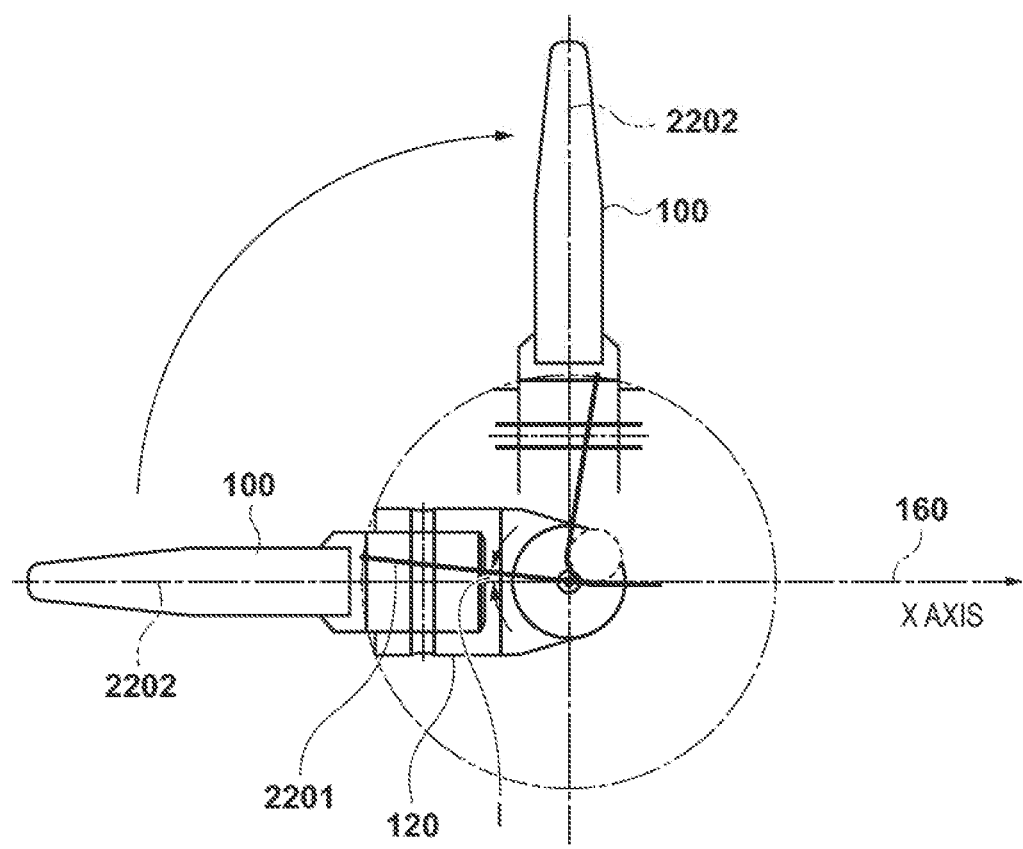
FIG. 22 is a view for explaining the offset angle of a wire.

Note that in the above-described example, the wire is arranged on the center line of the wrist member 120, and the position of the arc guide portion 144 (circle 601a) is obtained by setting, as the initial position of the wire, a state in which the wire matches the x-axis, that is, a state in which the wire is not in contact with the arc guide portion 144 (circle 601a) when the rotation angle (to be referred to as a pitch axis operation angle hereinafter) of the wrist member 120 about the pitch axis is 0°. However, the present invention is not limited to this. For example, it is sometimes difficult to arrange the wire on the center line of the wrist member 120 in terms of design because of, for example, the existence of a plurality of wires. As shown in FIG. 22, if the initial angle of a wire 2201 is offset from the x-axis by 1°, the position of the circular arc guide is appropriately corrected in accordance with the offset angle I. Note that the initial angle of the wire is an angle made by the wire and the x-axis when the angle made by the x-axis and a center line 2202 of the wrist member 120 is 0°. For example, if the offset I exists at the rotation position in the positive direction, as shown in FIG. 22, n in equations (2) or (4) is set to (n±I) in a case of positive-direction rotation or to (n−I) in a case of negative-direction rotation. If n swings in both the positive and negative sides, the average may be obtained as (n+I+n−I)/2=n. As described above, n in equations (2) or (4) is appropriately set almost within the range of |n|−|I| to |n|+|I|. That is, in equations (2), $x_a$ is set within the range of $(r_1/2)((|n|-|I|)/90) \leq x_a \leq (r_1/2)((|n|+|I|)/90)$. In equations (4), $x_a$ is set within the range of $1.3 \times (r_1/2)((|n|+|I|)/90) > x_a > (r_1/2)((|n|-|I|)/90)$. This enables design considering the offset of the wire.

If a plurality of wires exist, $x_a$ is appropriately set within the range of n−Imax° to n+Imax° in consideration of an average value Iaverage°, a maximum value Imax°, or a minimum value Imin° of the offset angles of the wires. Alternatively, if a plurality of wires exist, a circular arc guide with a different center position and/or diameter may be set for each wire. For example, in a structure using a plurality of flexible members to drive a plurality of driving portions (in this example, grippers), as shown in FIG. 1, the arc guide portions 144 may provide independent arc guide surfaces along the paths of the plurality of flexible members.

The medical manipulator 1 that is a robot forceps including the above-described end portion mechanism 10 will be described next with reference to FIGS. 9 to 11. The above-described end portion mechanism 10 is connected to the hollow shaft 20, and the hollow shaft 20 is connected to the operation unit 30. The hollow shaft 20 is a hollow shaft member capable of providing the paths of the first wire 161 to the third wire 163 inside. For example, if the first wire 161 to the third wire 163 may be exposed for an application purpose other than a medical application, the shaft member need not be hollow, and a structure other than a shaft may be used. The first wire 161 to the third wire 163 enter from the through holes 145 into the hollow shaft 20 and reach the operation unit 30.

The operation unit 30 is connected to the hollow shaft 20 and has an arrangement for generating, according to the user's operation, a force for the reciprocating operations of the first wire 161 to the third wire 163. In the operation unit 30, buttons 301 are operation switches configured to instruct driving of the wrist member 120 with respect to the pitch axis 132 as the center. That is, the reciprocating operation of the third wire 163 is performed by a motor 311 (9b in FIG. 9). Note that when the buttons 301 are arranged on the opposite side as well, the user can operate the buttons 301 by either of the left and right hands gripping the operation unit 30. A grip portion 302 is a member that the user can use to hold the medical manipulator 1. An operation lever 303 is a member used by the user to operate the rotation of the end effector 100 (including the opening/closing operation of the gripper) with respect to the yaw axis 131 as the center. The operation lever 303 can rotate in accordance with the user operation, and the force of the rotation operation to the operation lever 303 by the user is converted into the reciprocating operations of the first wire 161 and the second wire 162.

A storage portion 304 stores the motor 311 for driving the third wire 163 configured to rotate the wrist member 120, a control circuit (not shown) concerning driving of the motor, and a battery (not shown). Note that to reduce the weight, the battery and a part or whole of the control circuit may be arranged outside using cable connection. The control circuit includes, for example, a driving circuit configured to drive the motor, and a motor controller configured to instruct driving of the motor in accordance with the operation of the buttons 301. In addition, the storage portion 304 or the motor 311 may be detachable from the operation unit 30.

Figure 10:
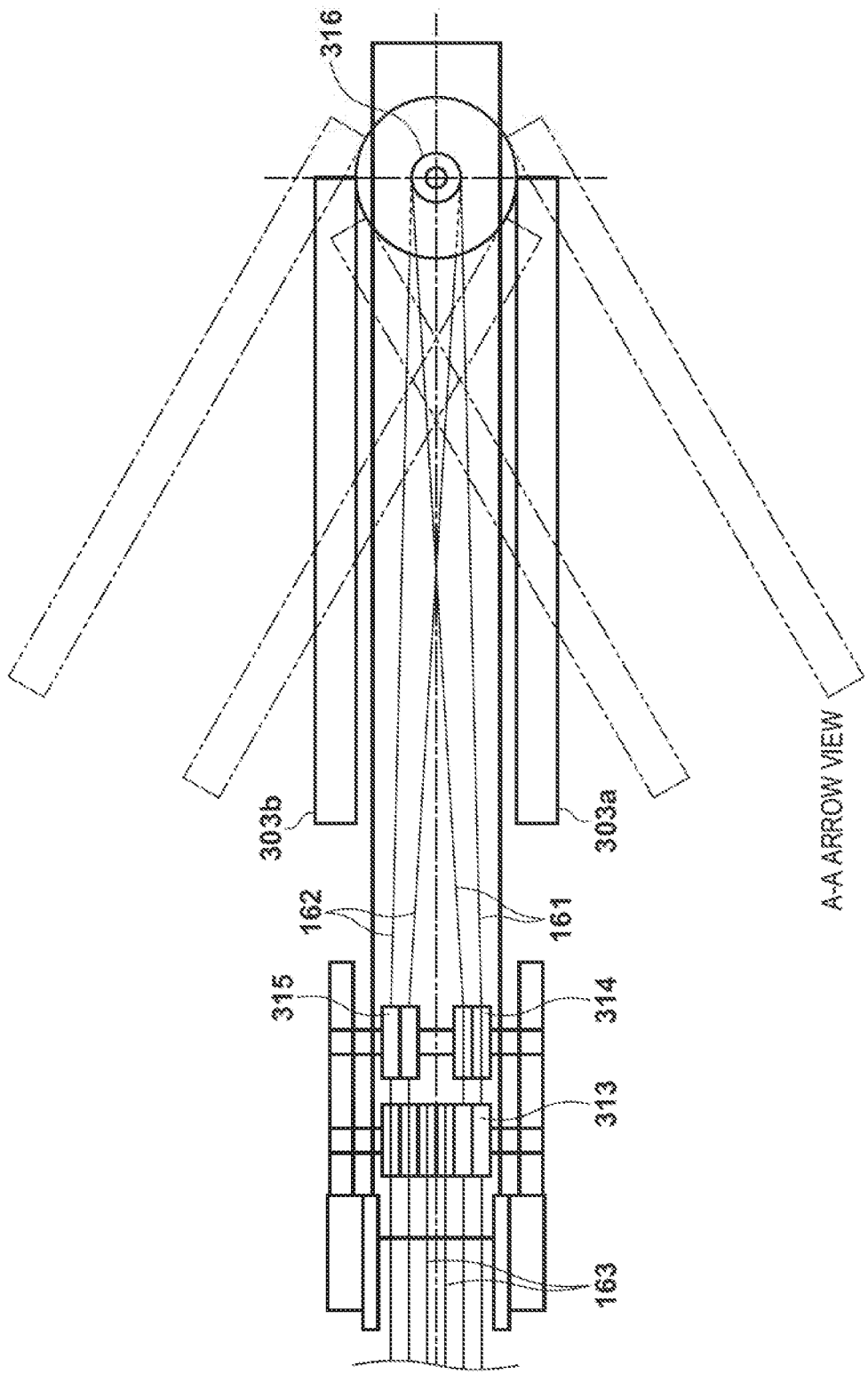
FIG. 10 is a schematic view of the medical manipulator viewed from the direction of A-A in FIG. 9.
Figure 11:
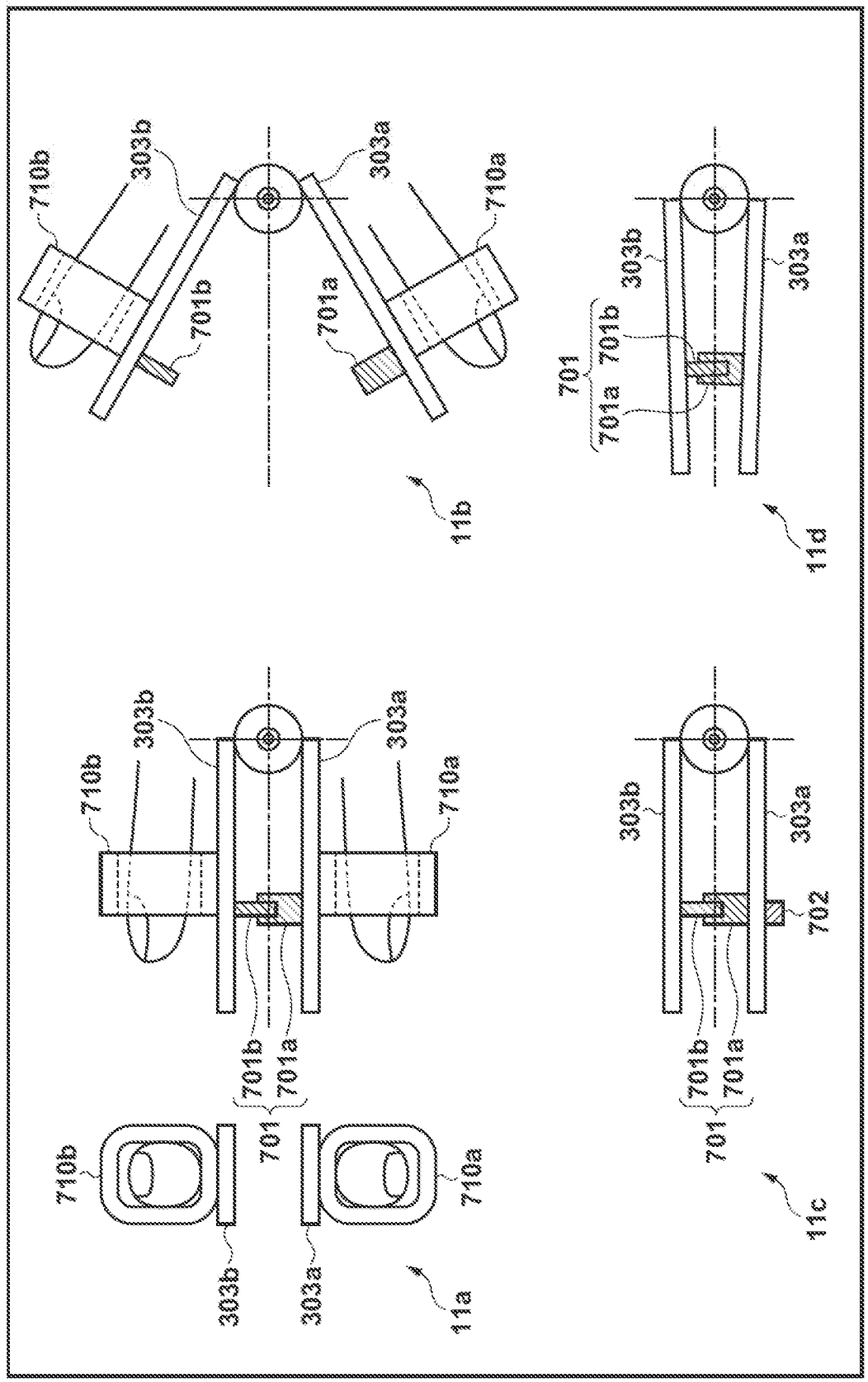
FIG. 11 is a schematic view for explaining the ratchet mechanism of the medical manipulator shown in FIG. 9.

As shown in FIGS. 9b and 10, a pulley 312 is attached to the driving shaft of the motor 311, and the third wire 163 is wound around the pulley 312. The direction of the third wire 163 is changed to the axial direction of the hollow shaft 20 by a pulley 313 and directed to the end portion mechanism 10. In this way, the motor 311 provides a driving force to rotate the wrist member 120 with respect to the connecting member 140. As shown in FIG. 10, the operation lever 303 is formed by a pair of operation levers 303a and 303b, and a pulley 316 rotates in accordance with the rotation operation of the operation lever 303a, and a pulley 317 rotates in accordance with the rotation operation of the operation lever 303b. The first wire 161 is wound around the pulley 316, passed through the hollow shaft 20 by a pulley 314 and the pulley 313, and directed to the end portion mechanism 10. Similarly, the second wire 162 is wound around the pulley 317, passed through the hollow shaft 20 by a pulley 315 and the pulley 313, and directed to the end portion mechanism 10. FIG. 10 schematically shows the arrangement of the pulleys 313, 314, and 315 viewed in the direction of A-A in FIG. 9b. In this way, the operation levers 303 and the pulleys 316 and 317 function as transmission members configured to transmit the operation force of the user as a driving force for the reciprocating operations to the first wire 161 and the second wire 162.

The user operates the buttons 301 while holding the grip portion 302, thereby performing rotation of the end effector 100 about the pitch axis. Note that a manual driving configuration may be formed in which a dial configured to manually rotate the pulley 312 is provided in place of the buttons 301 and the motor 311, and rotation of the wrist member 120 about the pitch axis is performed by a manual operation of the dial. In addition, rotation of the end effector 100 about the yaw axis can be performed by rotating the operation levers 303. For example, the opening/closing operation of one operation lever 303 is performed using a thumb, and the opening/closing operation of the other is performed by a forefinger. This makes it possible to open/close the gripper members 101 under an operation sensation similar to pinching them by the thumb and the forefinger, and give the user a more intuitive operation sensation. When the diameter ratio between the pulleys 316 and 317 and the wire guide portions 103a and 103b is changed, the opening/closing angle ratio between the operation levers 303 and the end effector 100 can be changed. That is, the opening/closing angle of the end effector 100 can be increased or decreased, and the operability improves. Note that in place of the operation levers 303, a motor configured to drive the pulley 316 and the pulley 317 may be provided to rotate the end effector 100 (rotate and open/close the gripper) about the yaw axis by a button operation.

Additionally, a ring-shaped member capable receiving a thumb, a forefinger, a middle finger, or the like may be added to each operation lever 303. This arrangement will be described with reference to 11a and 11b in FIG. 11. As shown in FIGS. 11a and 11b, when ring-shaped members 710a and 710b capable of receiving user's fingers are added to the operation levers 303a and 303b, respectively, the operation of opening/closing the operation levers 303 is facilitated. For example, when performing a tissue peeling operation using the end effector as a peeling forceps, a large peeling force can be transmitted to the end effector 100 as needed. Since the medical manipulator 1 can be held using the ring-shaped members 710, the operation unit 30 can also have a structure without the grip portion 302. Note that when using the medical manipulator 1 as a needle holder, a large peeling force is unnecessary. Hence, when a spring or the like that acts in a direction to always open the operation levers 303 is arranged, a curved needle can easily be handled.

A ratchet mechanism configured to maintain a close state may be provided on the operation levers 303a and 303b. The ratchet mechanism will be described with reference to 11a to 11d in FIG. 11. FIG. 11a shows a state in which the operation levers 303a and 303b are maintained in the close state by a ratchet mechanism 701. In this state, the gripper members 101a and 101b of the end effector 100 are maintained in the close state. The user can easily rotate the end effector 100 about the yaw axis in the close state of the gripper. FIG. 11b shows a state in which the maintaining state of the ratchet mechanism 701 is canceled, and the operation levers 303a and 303b are opened. In this state, the grip is also in an open state. As a mechanism configured to cancel maintaining of the close state by the ratchet mechanism 701, for example, a cancel button 702 as shown in FIG. 11c may be provided. Alternatively, for example, as shown in FIG. 11d, a mechanism that cancels the maintaining state of the ratchet mechanism 701 by further pushing the operation levers 303a and 303b in a direction to close may be used.

Note that in FIG. 9b, the pulley 312 may be decentered to the side of the hollow shaft 20. As described above, by the rotation operation about the pitch axis 132, the wire length error e is generated. If the wire length error e is positive, the first wire 161 and the second wire 162 contract. Basically, since the wires are in an expanded state by the initial tension, their postures change in a direction to contract. For example, if the wire length error e tends to be positive in a region where the absolute value of the pitch axis angle is small, the posture changes in a direction in which the absolute value of the pitch axis angle is large. Hence, in a state in which the absolute value of the pitch axis angle is small, the pulley 312 may be decentered to the distal end portion side (in FIG. 9b, to the side of the hollow shaft 20). When the pulley 312 is decentered in this way, the absolute value of the pitch axis angle becomes large, and the third wire 163 expands. Hence, the posture changes in a direction in which the absolute value of the pitch axis angle is small. Since the former situation in which the posture changes in the direction in which the absolute value of the pitch axis angle is large and the latter situation in which the posture changes in the direction in which the absolute value of the pitch axis angle is small can cancel each other, more stable control can be performed. Furthermore, if the rotation about the pitch axis is made not by motor driving but by manual driving, a larger effect can be obtained because it is associated with the direct operability of the user.

As described above, according to the medical manipulator 1 of the embodiment, the structures and shapes on the periphery of the wrist member 120 can be simplified by the structures of the through holes 145 and the arc guide portions 144, and the number of components can largely be reduced to reduce the cost. According to the medical manipulator 1, assembly is easy, and the assembling cost can also greatly be reduced. Additionally, it is possible to implement a non-interference driving mechanism in which the pitch axis operation does not actually affect the yaw axis operation. For this reason, the controllability of the medical manipulator 1 improves. In addition, the end effector (gripper) can be operated by the torque of a mechanical operation force of the user (surgeon), and a biotissue can delicately be handled. In particular, an operation of sandwiching a tissue or the like by the gripper can be performed by a manual operation of the user who is a surgeon, and the user can directly adjust the gripping force of the gripper. Furthermore, the offset amounts it the pitch axis and the yaw axis are reduced. When the medical manipulator is applied to a surgery supporting robot, an operation region including a wrist posture can be increased.

Note that in this embodiment, the gripping operation and the yaw operation of the gripper members 101 are performed by the user by operating the operation levers 303. Hence, an excessive load may be generated on the first wire 161 and the second wire 162. A member with an overload pi venting function, which deforms only when a predetermined load or more is applied to the driving system from the operation levers 303 to the gripper members 101, and returns to the initial state when the predetermined load is canceled, is preferably provided. An example of a structure that provides such an overload preventing function will be described below with reference to FIGS. 16 and 17. An example of an overload suppressing structure configured to deform when a load applied to a wire that is a flexible member has increased to a predetermined level or more to suppress the load applied to the wire to the predetermined level or less will be described below.

Figure 16:
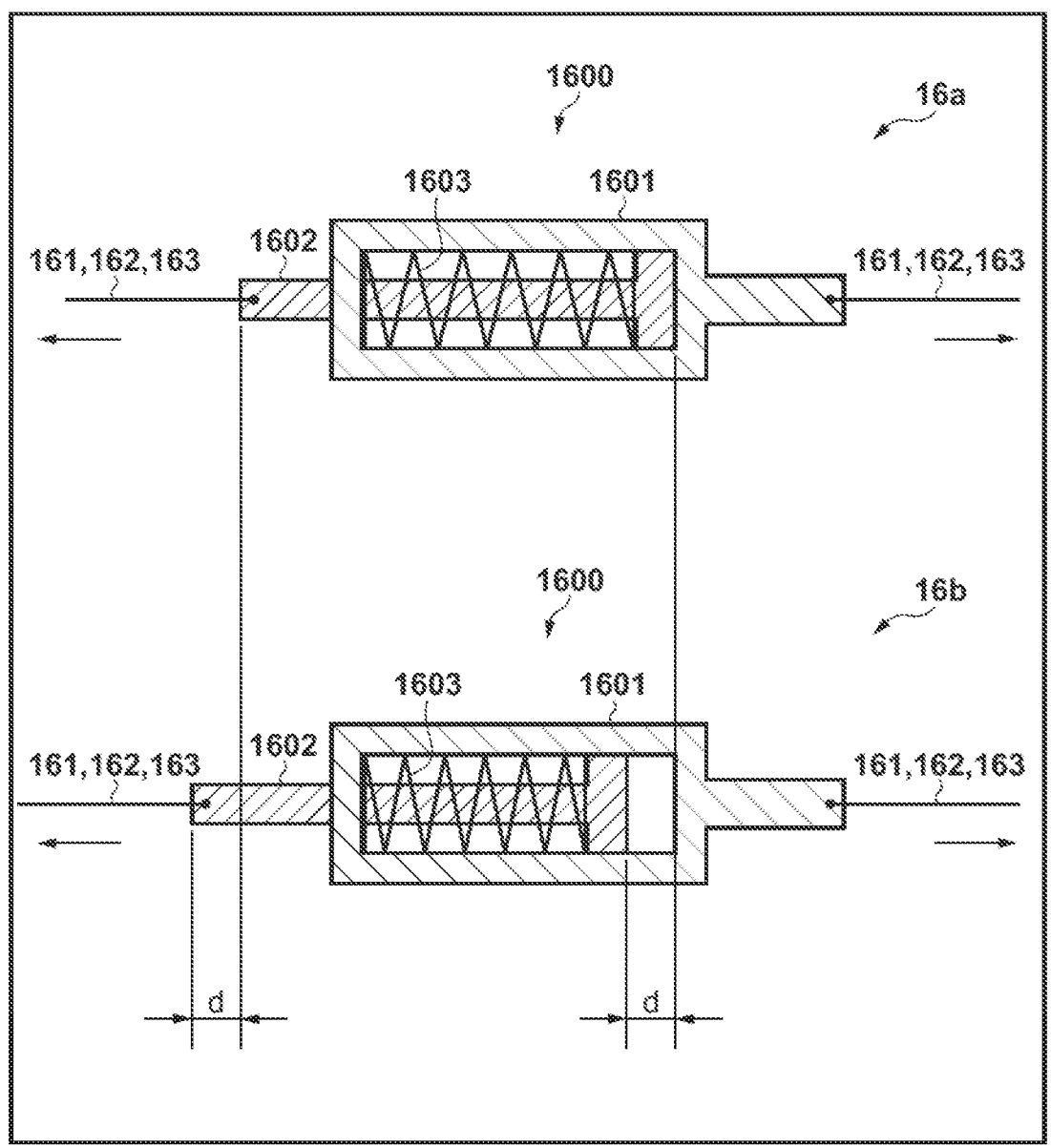
FIG. 16 is a view showing an arrangement example of an overload preventing mechanism.

FIG. 16 is a view showing an overload preventing portion 1600 applicable to each of the first wire 161 to the third wire 163 (to be referred to as wires hereinafter). The overload preventing portion 1600 includes a cylinder portion 1601, a piston portion 1602, and a spring 1603 serving as an elastic member. One end of the cylinder portion 1601 and one end of the piston portion 1602 are connected to wires to relay the wires. In a state shown in 16a of FIG. 16, the spring 1603 is stored in the cylinder portion 1601 while compressed by a predetermined force F. If a wire tension f is equal to or less than F (f≤F), the force of the spring 1603 to extend is larger. Hence, the state (a state in which the head portion of the piston portion 1602 is pressed against the cylinder portion 1601) shown in FIG. 16a is maintained. If the wire tension f exceeds F (f>F), the spring 1603 is further compressed and deformed such that the length of the overload preventing portion 1600 increases by d in accordance with the tension f, as shown in 16b of FIG. 16. If the wire tension f becomes equal to or less than F, the spring 1603 returns to the state in FIG. 16a again. As described above, when the overload preventing portion 1600 extends in accordance with the tension f, the tension applied to the wire is limited, and occurrence of wire cut is prevented. The predetermined force F is preferably equal to or more than the maximum tension within a normal use range and equal to or less than the breaking tension of the wire. Even in a state in which the overload preventing mechanism is acting, the tension f is preferably equal to or less than the breaking tension of the wire. Note that it is considered that overload preventing portions are arranged at two points on each wire. However, for example, if the overload state can be limited to the time of closing the gripper or the like, the overload preventing portion may be arranged only on the gripping operation side of each of the first wire 161 and the second wire 162.

FIG. 17 is a view showing another example of the overload preventing mechanism. In FIG. 17, each operation lever 303 is divided into a first lever 321 and a second lever 322, and these are connected by elastic members 720. The force of the finger of the user is applied to the first lever, and the gripper can be opened/closed in accordance with the operation farce of the user, as described above with reference to FIGS. 9 to 11. This state is shown in 17*a* of FIG. 17. However, if the gripper that is the end effector is to be closed by a force more than the predetermined force, the elastic member 720 bends. As shown in 17*b* of FIG. 17, the operation lever 303 deforms by bending at the connecting portion between the first lever 321 and the second lever 322, and the gripper cannot be closed by a force more than the predetermined force. Hence, an overload is not applied to the wire, and occurrence of wire cut or the like is prevented.

Figure 12:
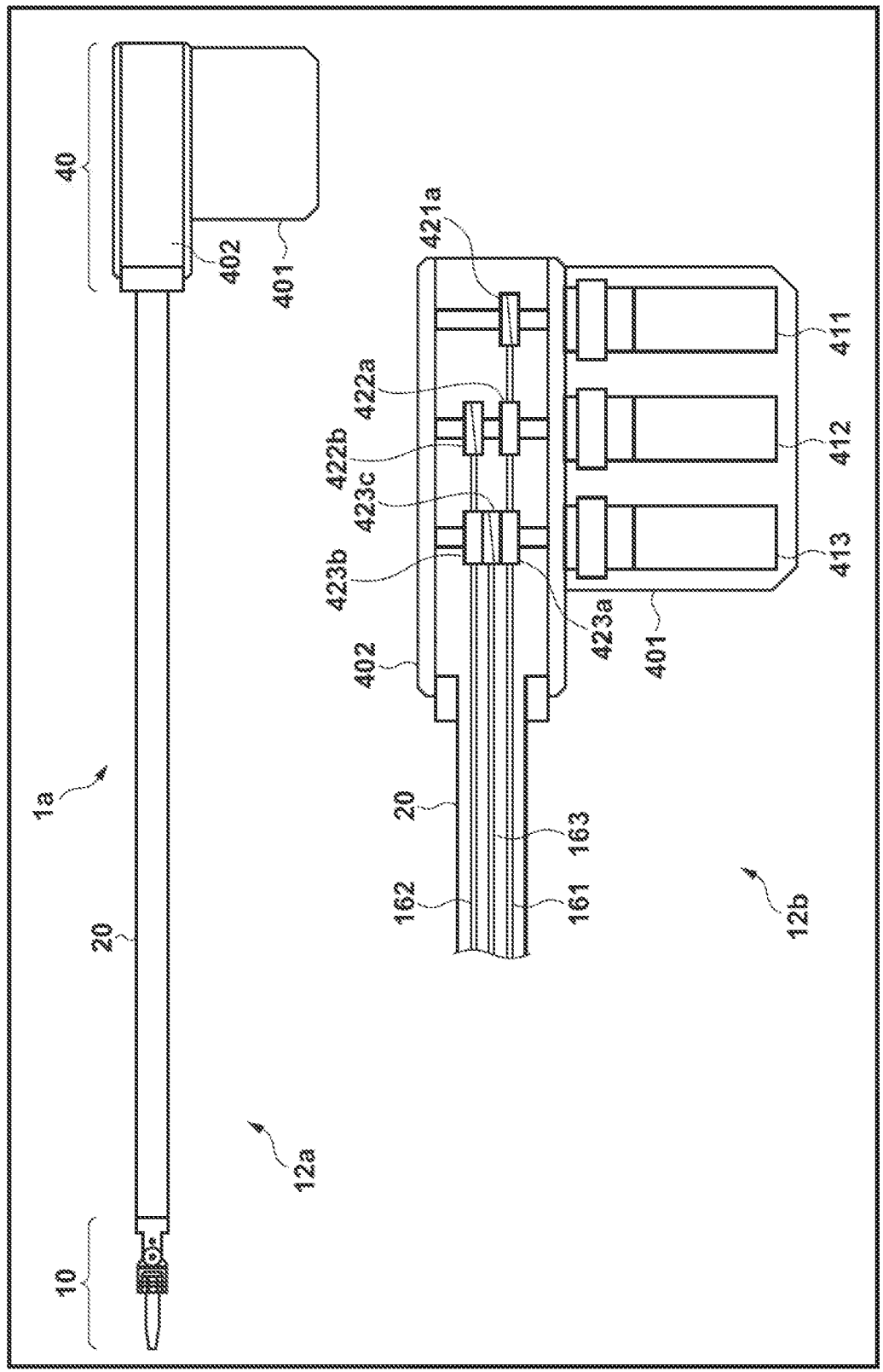
FIG. 12 shows a schematic view (12a) showing the outer appearance of the medical manipulator that drives all axes by motor driving and a schematic view (12b) showing an arrangement example of a driving unit.

A medical manipulator attachable to a medical robot in a surgery supporting robot system will be described next with reference to FIGS. 12 and 13. Note that the medical robot is not particularly limited, and can be any of a 6-axis vertical articulated arm, a 7-degree-of-freedom redundant articulated arm, and a polar coordinate arm with an immovable point mechanism in a trocar portion. An example of the surgery supporting robot system will be described later with reference to FIG. 15. In a medical manipulator to be used while attached to the medical robot, all the first wire 161 to the third wire 163 are driven by a motor. In FIG. 12, 12*a* is a view showing the outer appearance of a medical manipulator 1*a* in which all axes (the yaw axis (gripper axis) and the pitch axis) in the end portion mechanism 10 are driven by a motor. The medical manipulator 1*a* includes the end portion mechanism 10, the hollow shaft 20, and a driving unit 40. In the medical manipulator 1*a*, the operation unit 30 of the medical manipulator 1 (FIG. 9*a*) is replaced with the driving unit 40. The driving unit 40 includes a motor driving portion 401 and a pulley storage portion 402.

In FIG. 12, 12*b* is a view showing an internal arrangement example of the motor driving portion 401 and the pulley storage portion 402. The motor driving portion 401 includes a first motor 411 and a second motor 412, which are configured to rotate the pair of gripper members 101 of the end effector 100 about the yaw axis 131, and a third motor 413 configured to rotate the wrist member 120 about the pitch axis 132. A pulley 421*a* is fixed to the driving shaft of the first motor 411 and rotates together with the driving shaft. The first wire 161 is wound around the pulley 421*a*. A pulley 422*b* is fixed to the driving shaft of the second motor 412 and rotates together with the driving shaft. The second wire 162 is wound around the pulley 422*b*. A pulley 422*a* is rotatably attached to the driving shaft of the second motor 412 and guides the first wire 161. A pulley 423*c* is fixed to the driving shaft of the third motor 413 and rotates together with the driving shaft. The third wire 163 is wound around the pulley 423*c*. Pulleys 423*a* and 423*b* are rotatably attached to the driving shaft of the second rotor 412 and guide the first wire 161 and the second wire 162, respectively. Note that the pulley 422*a* and the pulleys 423*a* and 423*b* may be omitted if the wires and the driving shafts do not interfere. The motor driving portion 401 may be detachable from the pulley storage portion 402. Alternatively, the motor driving portion 401 may be arranged on the robot side, and the distal end portion side from the pulley storage portion 402 may be detachable from the robot. In this case, for example, the driving shafts of the first motor 411 to the third motor 413 and the pulleys 421 to 423 are detachably connected via couplings.

Figure 13:
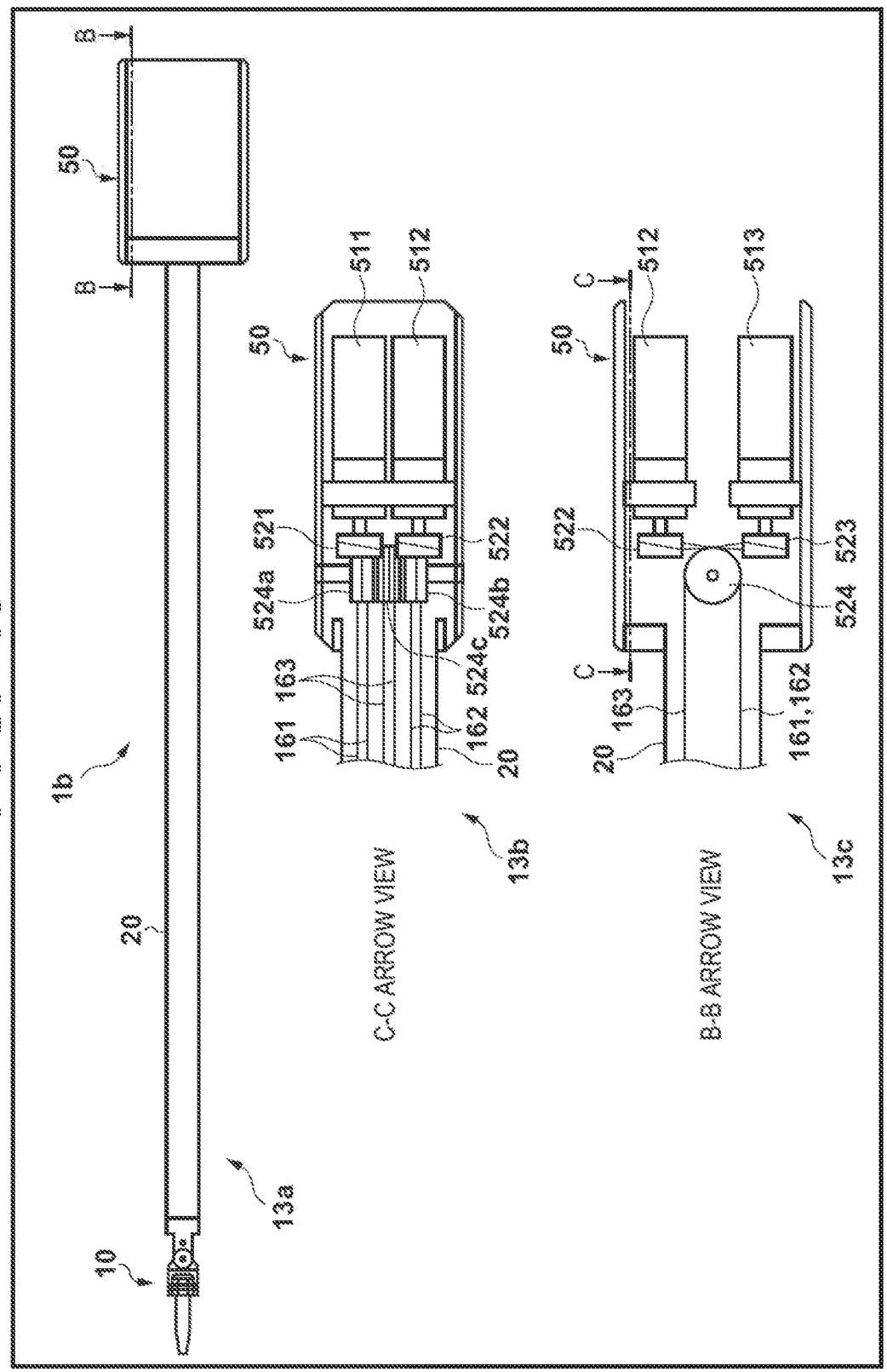
FIG. 13 shows a schematic view (13a) showing the outer appearance of another arrangement of the medical manipulator that drives all axes by motor driving and schematic views (13b and 13c) showing an arrangement example of the driving unit.

In FIG. 13, 13*a* is a view showing the outer appearance of a medical manipulator 1*b* in which all axes (the yaw axis (gripper axis) and the pitch axis) in the end portion mechanism 10 are driven by a motor. The medical manipulator 1*b* includes the end portion mechanism 10, the hollow shaft 20, and a driving unit 50. In the medical manipulator 1*b*, the operation unit 30 of the medical manipulator 1 (FIG. 9*a*) is replaced with the driving unit 50.

In FIGS. 13, 13*b* and 13*c* are views showing the internal arrangement of the driving unit 50. The driving unit 50 includes, in the inside, a first motor 511 and a second motor 512, which are configured to rotate the pair of gripper members 101 of the end effector 100 about the yaw axis 131, and a third motor 513 configured to rotate the wrist member 120 about the pitch axis 132. A pulley 521 is fixed to the driving shaft of the first motor 511. The first wire 161 is wound around the pulley 521, and the direction of the first wire 161 is changed to the axial direction of the hollow shaft 20 by a pulley 524*a*. A pulley 522 is fixed to the driving shaft of the second motor 512. The second wire 162 is wound around the pulley 522, and the direction of the second wire 162 is changed to the axial direction of the hollow shaft 20 by a pulley 524*b*. A pulley 523 is fixed to the driving shaft of the third motor 513. The third wire 163 is wound around the pulley 523, and the direction of the third wire 163 is changed via a pulley 524*c* such that it is directed to the end portion mechanism 10 along the axial direction of the hollow shaft 20. Note that as in FIG. 12, a portion including the first motor 511 to the third motor 513 and a portion including the pulleys 521 to 524 may be detachable. In this case, for example, the first motor 511 to the third motor 513 and the pulleys 521 to 523 are connected via couplings.

Figure 15:
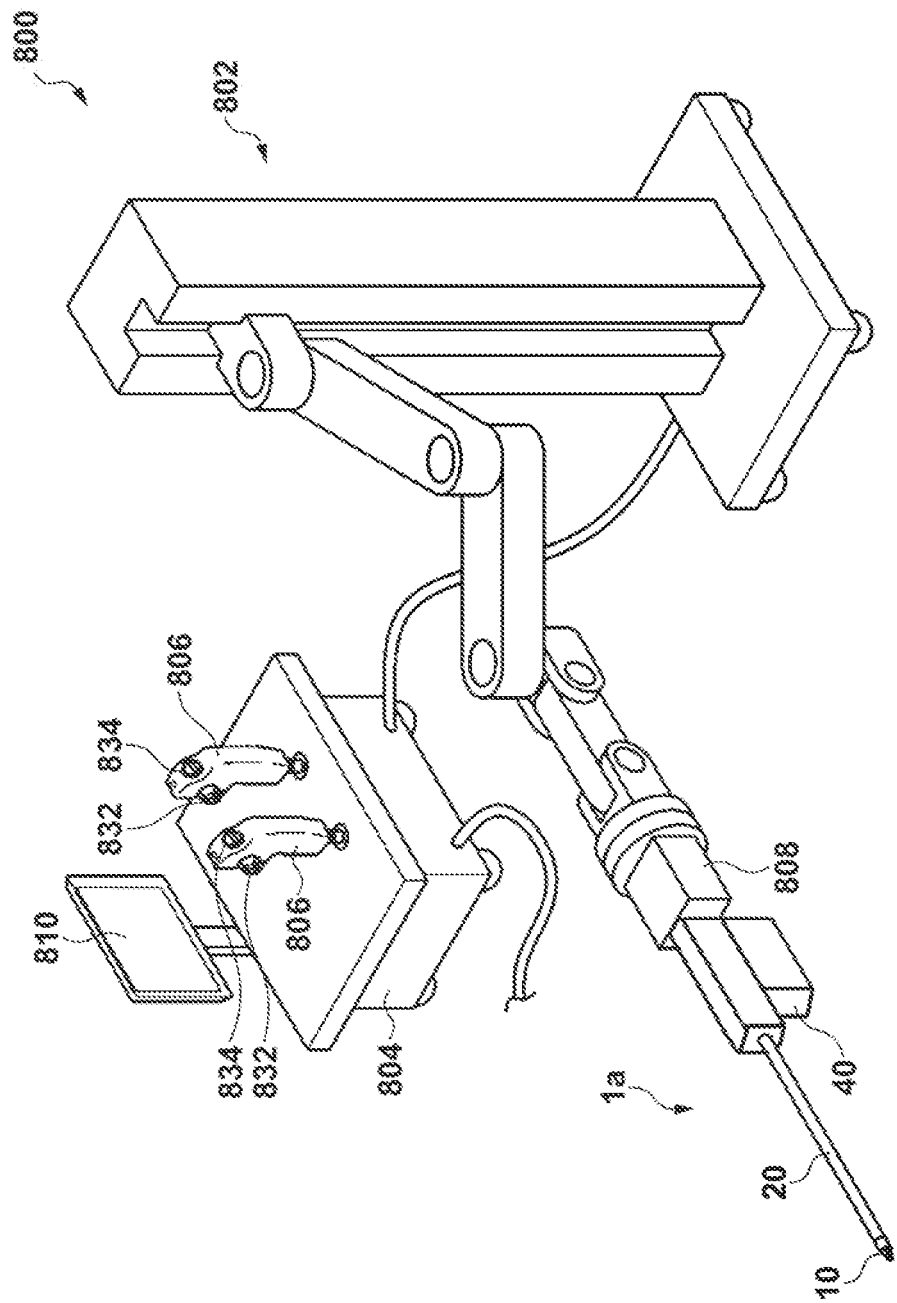
FIG. 15 is a view showing an arrangement example of a surgery supporting robot system.

The above-described medical manipulator 1*a* or 1*b* can be applied to, for example, a surgery supporting robot system 800 as shown in FIG. 15. An arrangement example of a surgery supporting robot system to which the medical manipulator 1*a* is applied will be described below. The surgery supporting robot system 800 includes a multi-freedom arm 802 that is an articulated robot arm as an example of a medical robot, and a console 804. The manipulator 1*a* is connected to the distal end of the multi-freedom arm 802. The multi-freedom arm 802 need only be a unit (means) for moving the manipulator 1*a*, and is not limited to a stationary type and may be of, for example, autonomous mobile type. The console 804 can employ a structure of a table type, a control panel type, or the like.

If the multi-freedom arm 802 includes six or more independent joints (rotation shafts, slide shafts, and the like), the position and direction of the manipulator 1*a* can arbitrarily be set. The manipulator 1*a* is integrated with a distal end portion 808 of the multi-freedom arm 802. The multi-freedom arm 802 operates under the control of the console 804, and may be configured to perform an automatic operation or semiautomatic operation by a program, remote control complying with joysticks 806 provided on the console 804, and a compound operation thereof. The console 804 is provided with the two joysticks 806 serving as an operation instruction portion and a monitor 810. Although not illustrated, two multi-freedom arms 802 can individually be operated by the two joysticks 806. The two joysticks 806 are provided at positions easy to operate by both hands. Information such as an image by a flexible scope is displayed on the monitor 810.

The joysticks 806 can perform an up-and-down operation, a left-and-right operation, a twisting operation, and a tilting operation and can move the multi-freedom arm 802 in accordance with these operations. The joysticks 806 may be master arms. A communication between the multi-freedom arm 802 and the console 804 can be realized by a wired communication, a wireless communication, a network, or a combination thereof. Each joystick 806 is provided with a trigger lever 832, and the rotation and opening/closing operation of the gripper can be performed by operating the trigger lever 832. Note that the trigger lever 832 may have a form like the operation lever 303 described with reference to FIGS. 9 to 11. A button switch 834 instructs an operation about the pitch axis. The button switch 834 may be switch separated in accordance with the moving direction, like the buttons 301 described with reference to FIGS. 9 to 11.

Note that the manipulator 1a has been described as a medical manipulator. However, the application purpose is not limited to this, and the manipulator can also be applied for an industrial application other than a medical application. For example, when the manipulator according to this embodiment is applied to a robot, a manipulator, and a distal end operation unit, which perform a repairing work or maintenance work requiring a gripping sensation or a large gripping force in a narrow part of an energy device or an energy facility or a place where a person cannot directly make a work, the same effects as described above can be obtained as a matter of course.

As described above, according to this embodiment, when the end portion mechanism 10 in which a mechanism interference is absent or is reduced to such a degree that the mechanism interference can be ignored is used, control concerning the mechanism interference is unnecessary when controlling the end portion mechanism 10 by motor driving. For this reason, if the manipulator 1a or 1b is used while attached to a medical robot, the end portion mechanism 10 can be easily be controlled. Additionally, as described above, the structure of the end portion mechanism 10 is extremely simplified, and the inexpensive medical manipulator 1a or 1b can be provided.

Note that in the above embodiment, a gripper is applied as the end effector 100. However, the present invention is not limited to this. For example, a probe may be applied as the end effector 100. In this case, one wire suffices as a wire used to rotate the end effector 100 about the yaw axis 131. In the above embodiment, a case in which the pitch axis 132 is used as a first rotation axis, and the yaw axis 131 is used as a second rotation axis has been described. However, the second rotation axis may be the pitch axis or a roll axis. Furthermore, another rotation axis may exist between the second rotation axis and the first rotation axis. In this case, to maintain the path length of a wire configured to drive a driven portion even if a member rotates about the other rotation axis, the portion of the other rotation axis is provided with the above-described arc guide portion. It is considered that the driven portion is not only the end effector described in the embodiment but also an arm member, a rotation axis support member, a power transmission member, or the like. The above-described joint mechanism applied to the end portion mechanism 10 can be applied to a joint mechanism at an arbitrary position of the manipulator.

Other Embodiment

An example of the medical manipulator 1 including the end portion mechanism 10, the hollow shaft 20, and the operation unit 30 has been described above with reference to FIGS. 9 to 11. In the above-described example, the grip portion 302 of the operation unit 30 is fixed to the hollow shaft 20. However, the present invention is not limited to this. Another arrangement example of the medical manipulator will be described with reference to FIGS. 18A and 18B. Note that the same reference numerals as in FIGS. 9 to 11 denote parts having similar functions in FIGS. 18A and 18B.

A hollow shaft 20 is a shaft member connected to an end portion mechanism 10 and including a hollow part that provides the outbound path and the returning path of each of a first wire 161, a second wire 162, and a third wire 163. An operation unit 30 includes an operation unit main body 1800 that supports the hollow shaft 20, and a handle portion 1801 attached to the operation unit main body 1800 to be rotatable about a yaw/gripper rotation axis 1802. The handle portion 1801 is thus connected to the operation unit main body 1800 to be rotatable about a rotation axis (yaw/gripper rotation axis 1802) almost orthogonal to the longitudinal direction of the hollow shaft 20 (shaft member). Since the handle portion 1801 is supported with respect to the operation unit main body 1800 to be rotatable about the yaw/gripper rotation axis 1802, the operability of a yaw axis operation or a gripper axis operation by an operator remarkably improves. The handle portion 1801 includes a grip portion 302 to be gripped by the user. A battery (not shown) that supplies power to a motor 311 configured to rotate a wrist member 120 (configured to perform a rotation operation about a pitch axis) can be stored in the grip portion 302. The motor 311 is stored in a storage portion 304. The motor 311 rotates a pulley 312 to drive the third wire 163, and consequently rotates the wrist member 120 about the pitch axis. A stopper 1811 is connected to the distal end of the pulley 312 to define the operation range of the wrist member 120 about the pitch axis. As in other embodiments, the motor 311 and the battery may be detachable.

An operation lever 303a is connected to a pulley 316, and the pulley 316 is rotated by operating the operation lever 303a. The rotation of the pulley 316 drives the first wire 161 and rotates a gripper member 101a (FIG. 1) on the left side about the gripper axis (yaw axis). Similarly, an operation lever 303b is connected to a pulley 317, and the pulley 317 is rotated by operating the operation lever 303b. The rotation of the pulley 317 drives the second wire 162 and rotates a gripper member 101b (FIG. 1) on the right side about the gripper axis (yaw axis).

The third wire 163 configured to drive the wrist member 120 about the pitch axis passes, from the end portion mechanism 10, through the hollow shaft 20 that is a forceps shaft, changes the wire path upward via a wire guide pulley 1814 of the operation unit main body 1800, and is wound around the pulley 312 of the operation unit main body 1800 basically not to slip. The pulley 312 is a pulley for pitch axis driving, which is connected to the motor 311 for pitch axis driving. The stopper 1811 is formed at the distal end portion of the pulley 312 to limit the operation range of the pitch axis. The diameters of the pulley 312 and a wire guide portion 125 of the end portion mechanism 10 are appropriately decided in accordance with the driving torque of the motor 311, the operation range of the pulley 312, and the like.

The driving power of the motor 311 is supplied from the battery (not shown) incorporated in the handle portion 1801 tin the grip portion 302) via a wire (not shown). Note that not only the battery but also an electric circuit, a microcomputer, a sensor, and the like may be stored in the handle portion 1801 as needed. A separate controller may be installed and connected via a cable or the like, as a matter of course.

Similarly, the first wire 161 and the second wire 162 configured to do driving about the yaw axis and the gripper axis pass, from the end portion mechanism 10, through the forceps shaft (through the hollow shaft 20), run via the wire guide pulley 1814 in the operation unit main body 1800, and are wound around the pulleys 316 and 317 for left and right gripper driving, which are arranged at the rear end portion of the operation unit main both 1800, basically not to slip. The pulley 316 for left gripper driving is integrated with the operation lever 303a that is an interface for a left gripper operation. The operation force/operation angle of the operator is transmitted to the pulley 316 via the operation lever 303a. The pulley 317 for the right gripper is connected, via a center shaft (not shown) arranged in the yaw/gripper rotation axis 1802, to the operation lever 303b that is an interface for a right gripper operation. The operation force/operation angle of the operator is transmitted to the pulley 317 for right g-ripper driving via the operation lever 303b and the center shaft. Note that the three components, that is, the pulley 317 for right gripper driving, the operation lever 303b, and the center shaft are connected by fixing them using set screws or the like.

The pulley 316 for left gripper driving and the operation lever 303a for the left gripper operation are integrated or connected to form a left gripper driving portion. The pulley 317 for right gripper driving, the center shaft (not shown), and the operation lever 303b for the right gripper operation are integrated or connected to form a right gripper driving portion. The operation unit main body 1800, the handle portion 1801, the left gripper driving portion, and the right gripper driving portion are connected to each other to be rotatable about the yaw/gripper rotation axis 1802. The yaw/gripper rotation axis 1802 matches the axis of the center shaft of the right gripper portion. In addition, the handle portion 1801, the left gripper driving portion, and the right gripper driving portion are connected via bearings, thereby enabling a smooth operation. As described above, in the medical manipulator 1 shown in FIGS. 18A and 18B, the forces of the rotation operations to the operation levers 303a and 303b that are rotatable in accordance with the operation of the user are converted into the reciprocating operations of the first wire 161 and the second wire 162, respectively. Here, the rotation axis of the operation levers 303a and 303b is coaxial with the yaw/gripper rotation axis 1802 configured to rotatably connect the operation unit main body 1800 and the handle portion 1801. As a result, a compact medical manipulator easy to use is provided.

Note that the diameters of the pulleys 316 and 317 for left and right gripper driving and a wire guide portion 103 of the end portion mechanism 10 are appropriately decided in accordance with the operation torque of the yaw/gripper axis, the operation range of the yaw/gripper axis, and the like. When the diameter of the pulleys 316 and 317 is made larger than the diameter of the wire guide portion 103, that is, when the speed is increased, the yaw/gripper axis can be driven in a small operation angle. This can reduce the operation angle of the wrist of the operator at the time of a yaw axis operation and improve the operability.

When the wire guide pulley 1814 is arranged on the distal end side of the operation unit main body 1800, that is, on the rear end side of the hollow shaft 20, the paths of the first wire 161, the second wire 162, and the third wire 163 can reliably and smoothly be guided to the corresponding pulleys. Note that the wire guide pulley 1814 may be not a rotatable pulley but an arc guide. In addition, the hollow shaft 20 is fixed to the operation unit main body 1800 by a split clamp portion 1812. Hence, the whole operation unit 30 and the hollow shaft 20 an be fixed in a state in which a predetermined wire tension is applied.

Figure 18A:
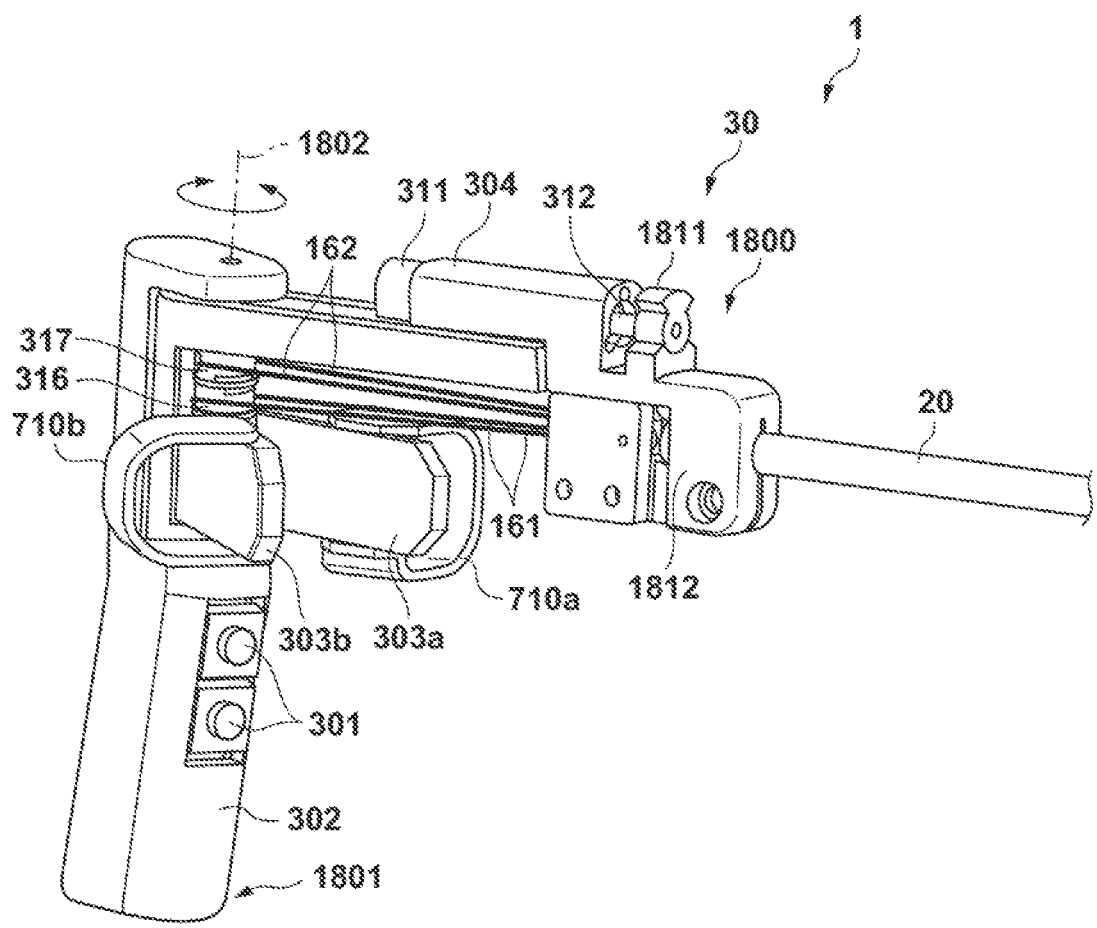
FIG. 18A is a view showing the outer appearance and the structure of a medical manipulator according to another example.

One or a plurality of wire guide members are arranged in the forceps shaft (20 hollow shaft). FIGS. 18A and 18B show one wire guide member 1813. When the first wire 161 to the third wire 163 are passed through holes provided in the wire guide member 1813, routing of the wires is facilitated, and twisting of the wires or assembly failures and troubles in driving caused by contacts can be reduced. In addition, the wire guide member 1813 can also be used as an airtight member.

By holding the handle portion 1801 (gripping the grip portion 302), the operator can stably hold the entire medical manipulator 1 and freely guide the position of the end portion mechanism 10 in the abdominal cavity of a patient as intended by the operator. The posture guide of the end portion mechanism 10 can be decided by rotation about the hollow shaft 20 caused by rotating the entire operation unit 30, that is, three posture axes including the roll axis, and the pitch axis and the yaw axis of the end portion mechanism 10. Furthermore, the gripper members 101 can be opened/closed by the gripper axis. Hence, in the position/orientation guiding method for the end portion mechanism 10, the pitch axis, the yaw axis, and the gripper axis separately need operation interfaces.

Pitch Axis Arrangement and Operation Method

A pitch axis operation can be performed by holding the handle portion 1801 and using buttons 301 each serving as a pitch axis operation interface arranged on the grip portion 302. For example, when the buttons 301 (for example, tactile switches) are arranged in the vertical diction on the front surface portion of the rotatable handle and configured such that the pitch axis operates upward when the upper button is pressed with the middle finger, and operates downward when the lower button is pressed with the third finger, a more intuitive operation can be performed. However, the finger used to operate is not particularly limited. In place of the tactile switch, a sliding switch, a joystick, a force sensor, or the like may be used as the button 301. In a non-operation state, the motor may be braked. Braking can be performed by control of holding the current angle by motor angle control or by short-circuiting the electrode of the motor. Also, a button used to return the pitch axis to the home position may be arranged on the grip portion 302.

Yaw Axis/Gripper Axis Arrangement and Operation Method

A yaw axis/gripper axis operation can be performed by holding the handle portion 1801 and using operation levers 303 each serving as a gripper operation interface. For example, when holding the handle portion 1801 by the right hand, the forefinger is inserted into an operation finger cover (member 710b) of the operation lever 303b as a right gripper operation interface, and the thumb is inserted into an operation finger cover (member 710a) of the operation lever 303a as a left gripper operation interface. When operating the yaw axis of the end portion mechanism 10, both the operation lever 303a and the operation lever 303b are rotated rightward or leftward with respect to the yaw/gripper rotation axis to rotate the pulleys 316 and 317 in the same direction, and the gripper members 101 operate in the yaw axis direction. At this time, since the handle portion 1801 is supported by the operation unit main body 1800 to be rotatable about the yaw/gripper rotation axis, the rotatable handle naturally rotates in accordance with the yaw axis operation of the operator and an angle without the sense of incongruity for the operator can be obtained. As a result, the operability remarkably improves. The rotation angle of the handle portion 1801 is preferably minimized within a range without hindrance for the yaw operation. That is, the rotation axis is preferably equal to the yaw axis angle of the left/right gripper operation interface.

When operating the gripper axis of the end portion mechanism 10, both the operation lever 303a and the operation lever 303b are rotated in directions opposite to each other with respect to the yaw/gripper rotation axis.

Accordingly, the pulley 316 and the pulley 317 are rotated in directions opposite to each other, and the gripper members 101 can be opened/closed. With the yaw axis/gripper axis arrangement and the operation, the motions of the wrist and fingers of the operator become the same as the yaw/gripper axis operation of the end portion mechanism 10, and an intuitive operation can be performed.

Figure 19A:
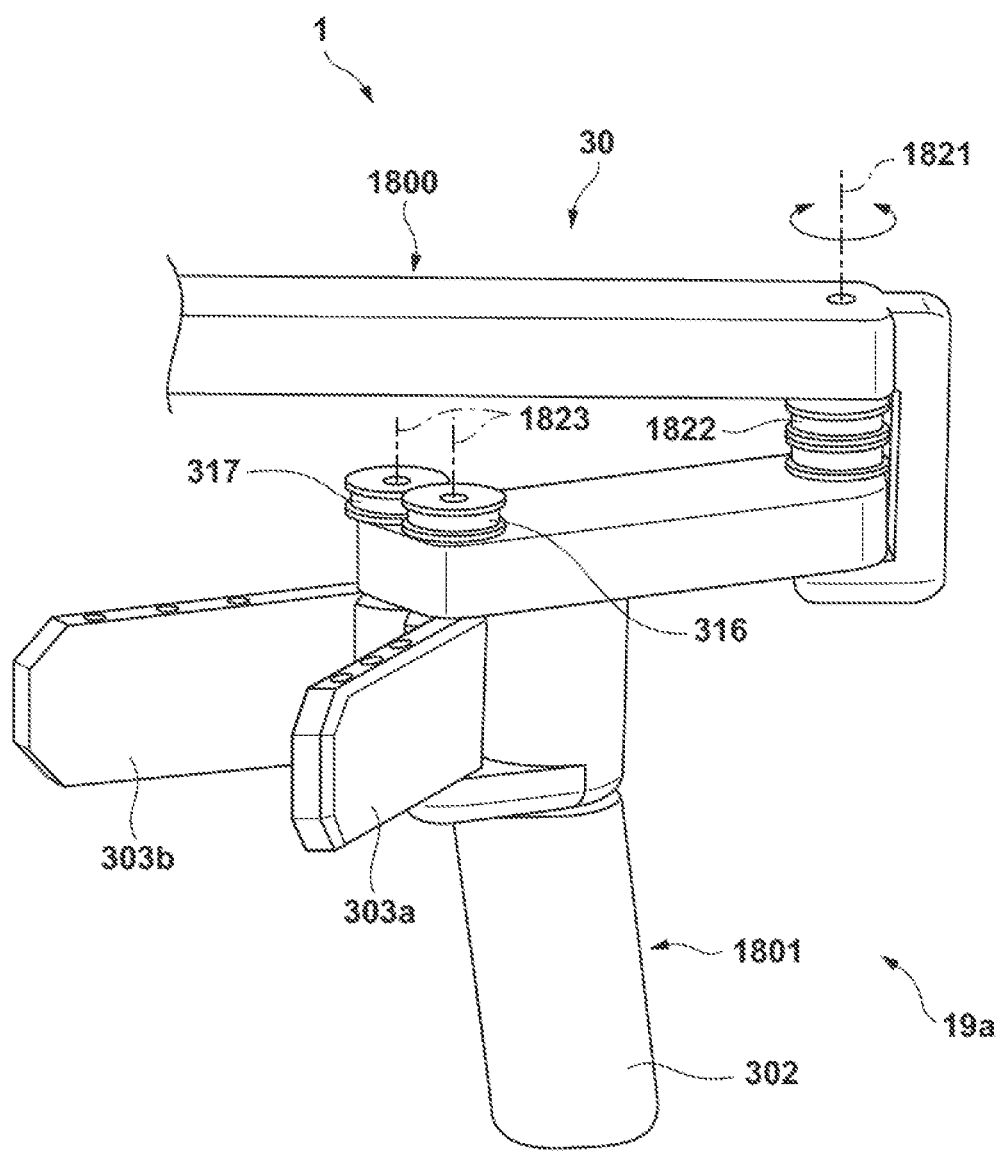
FIG. 19A is a view showing the outer appearance of a medical manipulator according to still another example.

FIG. 19A is a view showing still another form of the medical manipulator 1. FIG. 19A shows a part (rear end side) of the operation unit main body 1800 and the handle portion 1801 in the operation unit 30. The distal end side (the connecting portion to the hollow shaft 20, the arrangement for attaching the motor 311 for pitch axis driving, and the like) of the operation unit main body 1800 is the same as in FIGS. 18A and 18B. The handle portion 1801 is connected to the operation unit main body 1800 to be rotatable about a rotation axis (yaw axis rotation axis 1821) almost orthogonal to the longitudinal direction of the hollow shaft 20 (shaft member). Differences from the structure of the operation unit 30 described with reference to FIGS. 18A and 18B are that a yaw axis pulley 1822 is provided on the yaw axis rotation axis 1821, that the rotation axes (gripper axes 1823) of the operation levers 303a and 303b and the pulleys 316 and 317 are not coaxial with the yaw axis rotation axis 1821, and the arrangement/shape of the handle portion 1801.

Figure 19B:
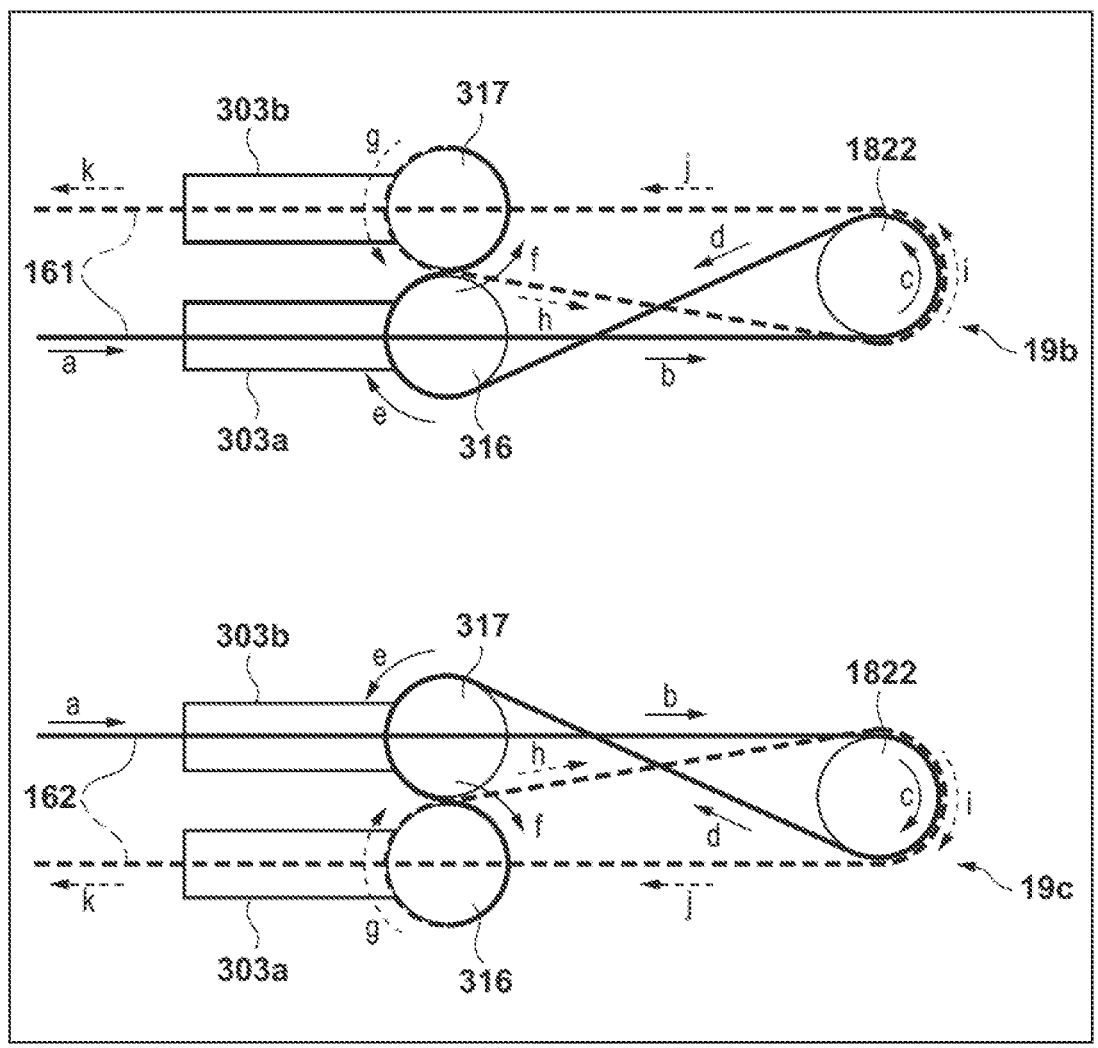
FIG. 19B is a view for explaining the path of a wire in the medical manipulator shown in FIG. 19A.
Figure 20:
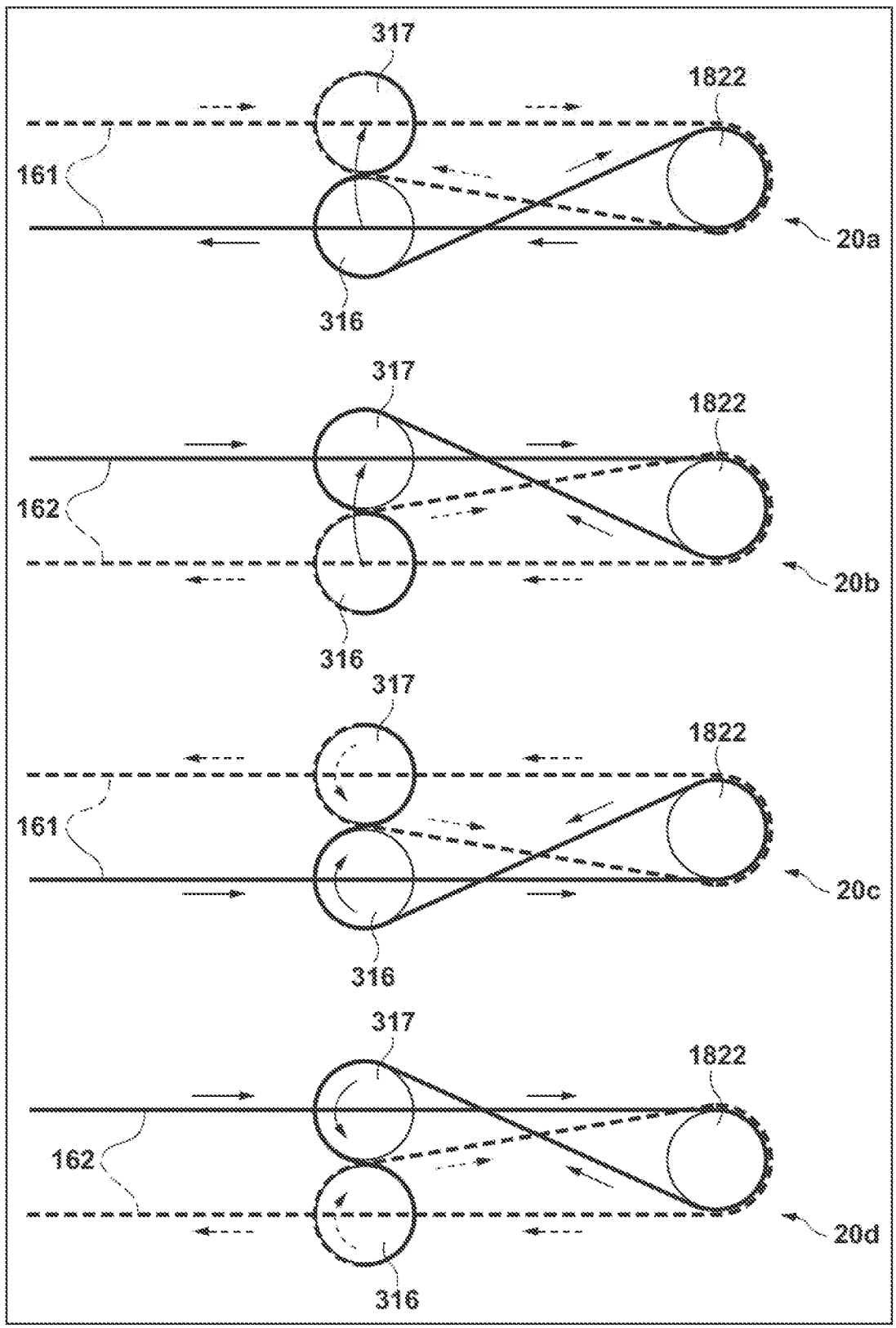
FIG. 20 is a view for explaining the operation of the wire in the medical manipulator shown in FIGS. 19A and 19B.

In FIG. 19B, 19b is a view for explaining the wound state of the first wire 161 around the pulley, and 19c of FIG. 19B is a view for explaining the wound state of the second wire 162 around the pulley. The first wire 161 and the second wire 162 are wound around the pulleys 316 and 317 and the yaw axis pulley 1822 in the order of arrows a to j as shown in FIGS. 19b and 19c. Additionally, in FIGS. 20, 20a and 20b show the motions of the first wire 161 and the second wire 162 when the handle portion 1801 is rotated about the yaw axis with respect to the operation unit main body 1800. By the wire winding method of this example, the left and right gripper members 101a and 101b rotate about the yaw axis in a state in which their open/close state (angle) is maintained. In addition, 20c and 20d of FIG. 20 show the motions of the first wire 161 and the second wire 162 when the operation levers 303a and 303b are rotated about the gripper axes 1823. In this case, the rotation operations of the left and right gripper members 101a and 101b with respect to the gripper axis synchronize with each other, and the left and right gripper members 101a and 101b always open by the same angle with respect to a center axis 133 (FIG. 1). Note that winding of the wires may be simplified by arranging a pair of gears on the pulley 316 and the pulley 317 and making them synchronize.

As described above, in the medical manipulator 1 shown in FIG. 19A, the yaw axis rotation axis 1821 that rotatably connects the operation unit main body 1800 and the handle portion 1801 is located at a position farther from the hollow shaft 20 than the rotation axes (gripper axes 1823) of the operation levers 303a and 303b. According to this arrangement, the yaw axis operation and the gripper axis operation can be separated. In addition, since the yaw axis rotation axis 1821 and the wrist joint axis of the operator are close, the yaw axis operation can be performed more intuitively. Furthermore, the medical manipulator 1 includes the pulley 316 connected to the operation lever 303a, the pulley 317 connected to the operation lever 303b, and the yaw axis pulley 1822 that rotates about the yaw axis rotation axis 1821, and the first wire 161 and the second wire 162 are wound around the pulleys such that the pair of gripper members 101a and 101b synchronize. As a result, it is possible to easily open/close the distal end of the gripper at a desired position and improve the operability.

In the above-described the medical manipulator 1, the operation unit 30 and the hollow shaft 20 are fixed, and rotation about the roll axis is implemented by the operator manually rotating the operation unit 30. However, the arrangement of the medical manipulator 1 is not limited to this, and, for example, rotation about the roll axis may be implemented by motor driving.

Figure 21:
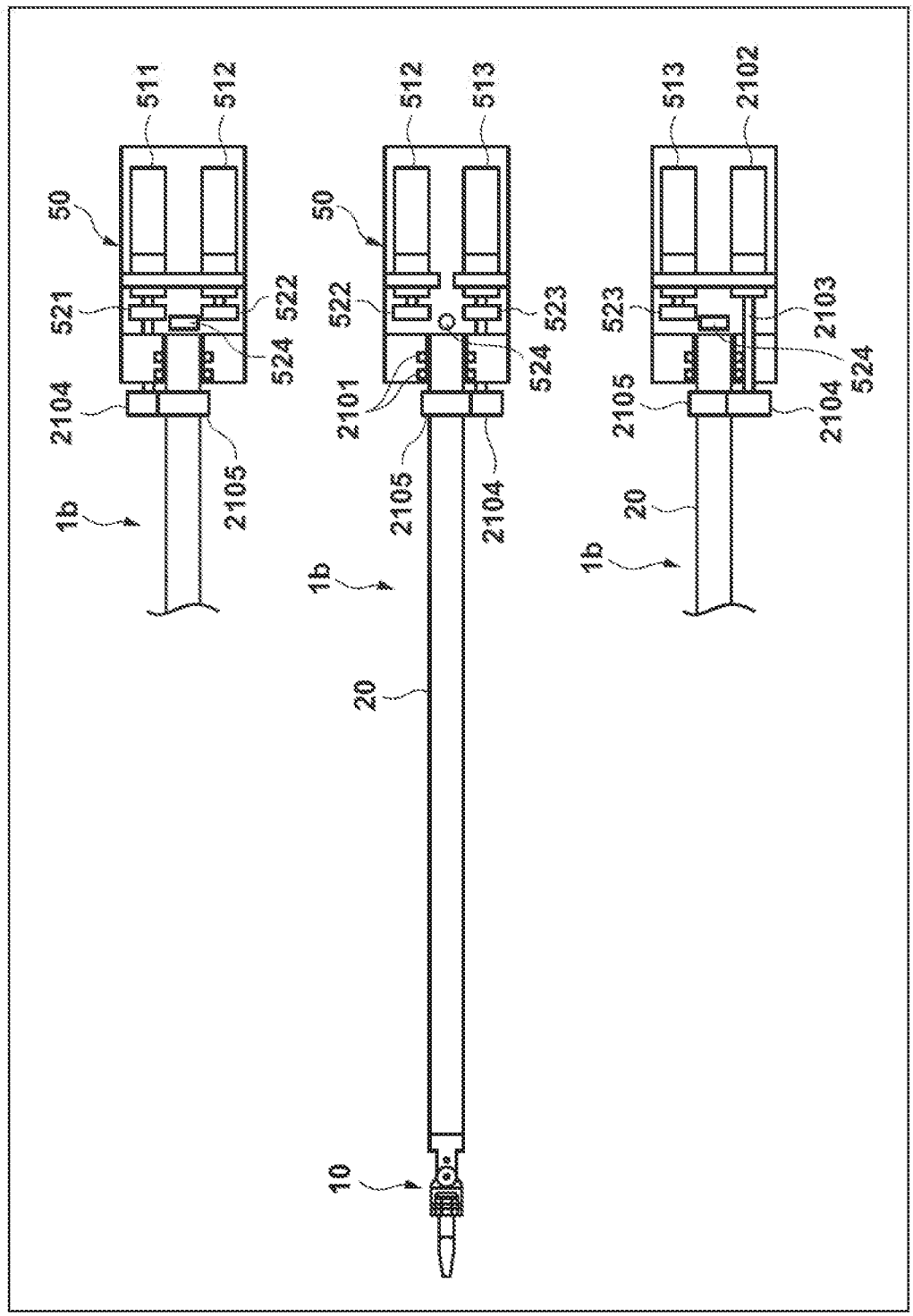
FIG. 21 is a view showing an arrangement example of a medical manipulator capable of rotating about a roll axis.

In FIG. 21, a motor 2102 for roll axis driving is added to the medical manipulator 1b described with reference to FIG. 13 in which all axes (the yaw axis (gripper axis) and the pitch axis) in the end portion mechanism 10 are driven by a motor. The hollow shaft 20 is connected to a driving unit 50 via bearings 2101, and the hollow shaft 20 is held rotatably with respect to the driving unit 50. A gear 2104 is provided at the distal end of a motor shaft 2103 of the motor 2102. The gear 2104 meshes with a gear 2105 provided on the hollow shaft 20. When the motor shaft 2103 is rotated by driving of the motor 2102, the gear 2104 rotates, and the gear 2105 rotates. This implements the rotation of the hollow shaft 20 about the roll axis.

Figure 23:
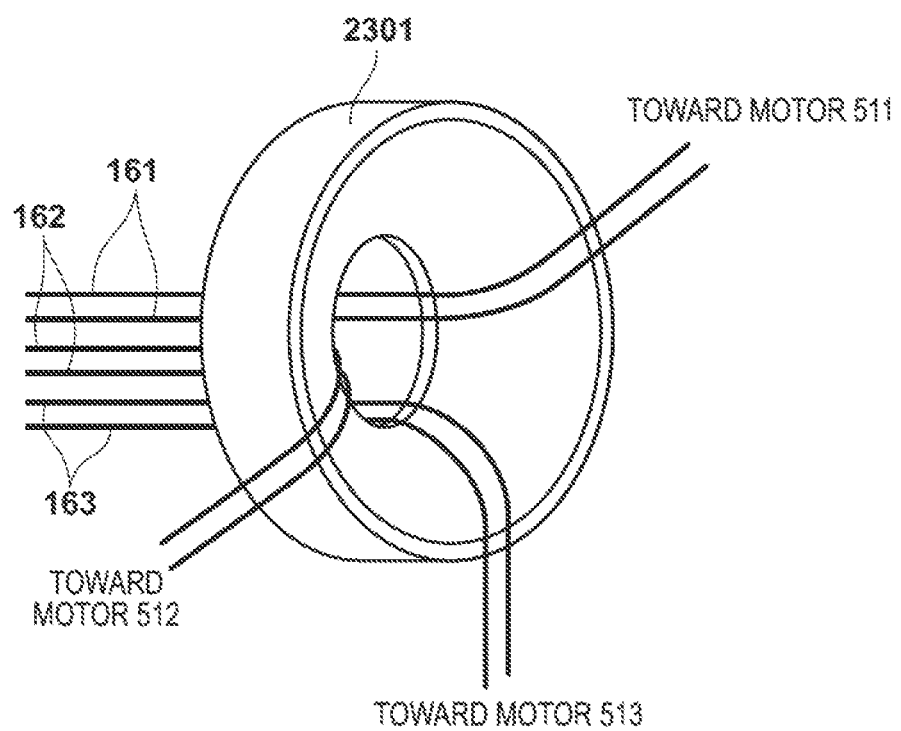
FIG. 23 is a view showing an example of a guide portion that replaces a wire guide pulley.

In place of the pair of gears 2104 and 2105, a power transmission member such as a belt or a wire may be used. To change the directions of the first wire 161, the second wire 162, and the third wire 163, a pulley 524 as described with reference to FIG. 13 (or having a function of changing the direction of a wire, like the wire guide pulley 1814 shown in FIG. 18B) may be used, or a circular arc guide 2301 as shown in FIG. 23 may be used. In the circular arc guide 2301, a surface that connects a through hole at the center and a peripheral wall portion is formed by an arc of a predetermined diameter, and the directions of the first wire 161 to the third wire 163 are changed toward the pulleys of corresponding motors. Note that the arc surface of the circular arc guide 2301 is not limited to a circular arc, and an elliptical arc or the like may be used.

Figure 24:
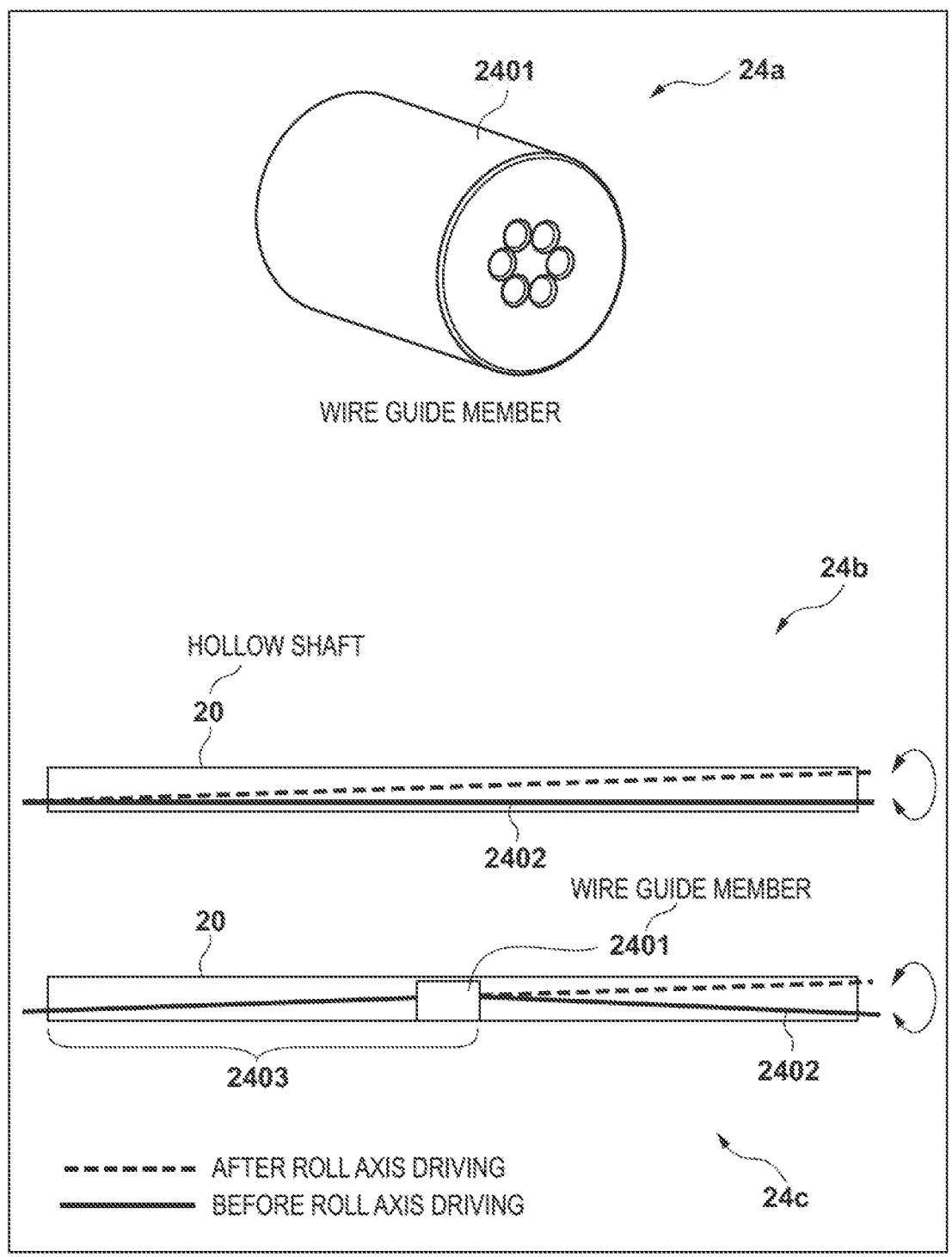
FIG. 24 is a view showing another example a a wire guide member.

Additionally, as in the arrangement described above with reference to FIGS. 12 and 13, motors 511, 512, 513, and 2102 and pulleys 521, 522, and 523, and the motor shaft 2103 may be detachable to separate the driving unit 50. A stopper configured to limit the operation angle as needed, an encoder configured to detect the motor rotation angle or speed, an origin sensor, and the like may be incorporated. In this embodiment, when the roll axis is driven, the first wire 161, the second wire 162, and the third wire 163 twist, and the path lengths of the wires slightly change. Hence, a wire guide member 2401 as shown in 24a of FIG. 24, in which holes to pass the wires are arranged near the center, may be arranged near the intermediate point of the hollow shaft 20. For example, as shown in 24b of FIG. 24, the path of a wire 2402 changes from a path indicated by a solid line to a path indicated by a broken line by roll axis driving. When the wire guide member 2401 is arranged, the change of the path caused by roll axis driving rarely occurs in a section 2403 up to the position where the wire guide member 2401 is arranged, as shown in 24c of FIG. 24. On the distal end side of the wire guide member 2401, the path of the wire 2402 changes from a path indicated by a solid line to a path indicated by a broken line. Hence, according to this arrangement, it is possible to suppress the change of the wire path length and avoid troubles caused by twist or contact of the wire.

As described above, according to the embodiments of the present invention, the occurrence of a mechanism interference in a driven portion driven by a reciprocating operation of a wire is reduced or eliminated.

The present invention is not limited to the above embodiments, and various changes and modifications can be made within the spirit and scope of the present invention. Therefore, to apprise the public of the scope of the present invention, the following claims are made.

What is claimed is:

1. A manipulator comprising:
    a first member;
    a second member configured to support the first member such that the first member can rotate about a first rotation axis;
    a driven portion connected to the first member and configured to move on a circumference with respect to the first rotation axis as a center in accordance with a rotation operation of the first member;
    a flexible member configured to provide, by a reciprocating operation, a force to drive the driven portion; and
    a change unit including an arc guide surface configured to change a path of the flexible member in accordance with the rotation operation of the first member,
    wherein the arc guide surface comprises a surface having a circular arc shape, and
    wherein on a coordinate system for which, on a plane perpendicular to the first rotation axis, a position of the first rotation axis is defined as an origin, and axes that pass the origin and are orthogonal to each other are defined as an x-axis and a y-axis, letting $r_1$ be a sum of a radius of the circular arc shape and a radius of the flexible member, coordinates ($x_a$, $y_b$) of a center position of the circular arc shape are given by $x_a \geq (r_1/2)$ $-r_1 \leq y_b \leq r_1$.

2. The manipulator according to claim 1, wherein the coordinates ($x_a$, $y_b$) of a center position of the circular arc shape are given by $1.3 \times (r_1/2) > x_a > (r_1/2)$ $0.7 \times r_1 < y_b < r_1$ or $-0.7 \times r_1 > y_b > -r_1$.

3. The manipulator according to claim 1, further comprising a shaft member connected to the second member, wherein the x-axis matches a center axis of the shaft member in a longitudinal direction.

4. The manipulator according to claim 1, wherein the change unit includes the arc guide surfaces to sandwich a plane including the x-axis and the first rotation axis from upper and lower sides.

5. The manipulator according to claim 1, wherein the driven portion includes a plurality of driving portions,
    the flexible member includes a first flexible member and a second flexible member configured to drive the plurality of driving portions, and
    the change unit provides independent arc guide surfaces along paths of the first flexible member and the second flexible member.

6. The manipulator according to claim 1, wherein the driven portion is supported, with respect to the first member, to be rotatable about a second rotation axis different from the first rotation axis.

7. The manipulator according to claim 6, wherein the second rotation axis is orthogonal to a plane including the first rotation axis.

8. The manipulator according to claim 6, wherein the driven portion includes a pair of gripper members, and the flexible member includes a first flexible member and a second flexible member configured to individually rotate the pair of gripper members about the second rotation axis.

9. The manipulator according to claim 1, wherein the second member includes a communicating portion configured to make a side of supporting the first member communicate with an opposite side and provide a part of a path of the flexible member, and
    the change unit forms a part of the communicating portion.

10. The manipulator according to claim 9, wherein the communicating portion includes through holes separately provided in the second member in correspondence with an outbound path and a returning path in the reciprocating operation of the flexible member, and the through holes are arranged in parallel to the first rotation axis.

11. The manipulator according to claim 10, wherein the through holes have airtightness capable of maintaining a pneumoperitoneum pressure of 5 to 20 mmHg in a state in which the flexible member is inserted.

12. The manipulator according to claim 1, further comprising a third flexible member configured to transmit, by a reciprocating operation, a force to rotate the first member about the first rotation axis with respect to the second member.

13. The manipulator according to claim 12, wherein an outbound path and a returning path of the third flexible member pass into through holes provided in the second member, and the through holes have airtightness capable of maintaining a pneumoperitoneum pressure of 5 to 20 mmHg in a state in which the third flexible member is inserted.

14. A surgery supporting robot system comprising:
    a manipulator described in claim 1;
    a multi-freedom arm to which the manipulator is attached; and
    a control unit configured to control the multi-freedom arm and the manipulator automatically, semiautomatically or by remote control.

15. The manipulator according to claim 1 A manipulator comprising:
    a first member;
    a second member configured to support the first member such that the first member can rotate about a first rotation axis;
    a driven portion connected to the first member and configured to move on a circumference with respect to the first rotation axis as a center in accordance with a rotation operation of the first member;
    a flexible member configured to provide, by a reciprocating operation, a force to drive the driven portion; and
    a change unit including an arc guide surface configured to change a path of the flexible member in accordance with the rotation operation of the first member,
    wherein the arc guide surface comprises a surface having a circular arc shape, and is arranged to maintain a path length of the flexible member in the reciprocating operation during the rotation operation of the first member,
    wherein on a coordinate system for which, on a plane perpendicular to the first rotation axis, a position of the first rotation axis is defined as an origin, and axes that pass the origin and are orthogonal to each other are defined as an x-axis and a y-axis, letting $r_1$ be a sum of a radius of the circular arc shape and a radius of the flexible member, letting n° be a maximum angle of the rotation operation of the first member about the first rotation axis with respect to the x-axis and I° be an angle made by the flexible member and the x-axis when n=0, the coordinates ($x_a$, $y_b$) of the center position of the circular arc shape are given by $x_a(r_1/2)(|n|/90)$ and $y_b = r_1$ or $-r_1$   (i).

$(r_1/2)((|n|-|I|)/90) \leq x_a \leq (r_1/2)((|n|+|I|)/90)$ and $y_b = r_1$ or $-r_1$   (ii).

$1.3 \times (r_1/2)(|n|/90) > x_a > (r_1/2)(|n|/90)$ and $0.7 \times r_1 > y_b > r_1$ or $-0.7 \times r_1 > y_b > -r_1$   (iii).

$1.3 \times (r_1/2)((|n|+|I|)/90) > x_a > (r_1/2)((|n|-|I|)/90)$ and $0.7 \times r_1 < y_b < r_1$ or $-0.7 \times r_1 > y_b > -r_1$   (iv).

\* \* \* \* \*